(12) United States Patent
Benz et al.

(10) Patent No.: US 8,106,146 B2
(45) Date of Patent: Jan. 31, 2012

(54) THERAPEUTIC POLYMERS AND METHODS OF GENERATION

(75) Inventors: Michael E. Benz, Ramsey, MN (US); Erica M. Tenbroek, Roseville, MN (US); Lian Leon, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 98 days.

(21) Appl. No.: 12/766,676

(22) Filed: Apr. 23, 2010

(65) Prior Publication Data

US 2011/0082266 A1  Apr. 7, 2011

Related U.S. Application Data

(60) Provisional application No. 61/249,098, filed on Oct. 6, 2009.

(51) Int. Cl.
*C08G 63/02* (2006.01)
*C08G 63/00* (2006.01)

(52) U.S. Cl. .............. 528/205; 424/78.38; 424/423; 424/484; 514/282; 514/299

(58) Field of Classification Search ............. 424/78.38, 424/423, 484; 514/282, 299
See application file for complete search history.

(56) References Cited

U.S. PATENT DOCUMENTS 4,513,143 A  4/1985  Ng et al.
4,532,335 A  7/1985  Helwing

OTHER PUBLICATIONS

Bove, et al., "Weight bearing as a measure of disease progression and efficacy of anti-infammatory compounds in a model of monosodiu, iodoacetate-induced osteoarthritis" Osteoarthritis Cartilage, 11(11):821-830; 2003.
Bove, et al, "Surgically induced osteoarthritis in the rat results in the development of both osteoarthritis-like joint pain and secondary hyperalgesia," Osteoarthritis Cartilage, 14(10)1041-1048, 2006.
Crivello, et al., "Ketene Acetal Monomers—Synthesis and Characterization", Journal of Polymer Science Part A: Polymer Chemistry, 34(15):3091-3102, 1996. Unable to Locate Copy.
Ng, et al., "Poly (Ortho Esters) by the Addition of Diols to a Diketene Acetal", Macromolecular Syntheses, 11:23-26; 1992. Unable to Locate Copy.
Ng, et al., "Development of a poly(ortho ester) prototype with a latent acid in the polymer backbone for 5-fluorouracil delivery" Journal of Controlled Release, 65(3):367-374; Apr. 2000.
Pogany, et al., "Gas chromatographic assay for 3,9-diethylldent-2,4,8,10 tetraoxaspiro[5.5]undecane" Journal of Chromatography, 508:179-166; 1900. Unable to Locate Copy.
Honokee, Sah, "Microencapsulation techniques using ethyl acetate as a dispersed solvent: effects of its extraction rate on the characteristics of PLGA microspheres" Journal of Controlled Release, 47:233-245, 1997.

*Primary Examiner* — Terressa Boykin
(74) *Attorney, Agent, or Firm* — Jeffrey J. Hohenshell

(57) ABSTRACT

The invention describes poly(ortho ester) polymers that include at least one therapeutic compound in the polymer backbone. The therapeutic compound includes at least one phenol residue and an aliphatic alcohol residue or two or more phenolic residues.

20 Claims, 5 Drawing Sheets

THERAPEUTIC POLYMERS AND METHODS OF GENERATION

CROSS REFERENCE TO RELATED APPLICATIONS

This application claims priority to U.S. provisional patent application Ser. No. 61/249,098, titled "Therapeutic Polymers and Methods of Generation", filed on Oct. 6, 2009, the contents which are hereby incorporated by reference in their entirety.

FIELD OF THE INVENTION

The invention relates generally to poly(ortho ester) polymers that include at least one therapeutic compound in the polymer backbone. The therapeutic compound includes at least one phenol residue and an aliphatic alcohol residue or two or more phenolic residues.

BACKGROUND OF THE INVENTION

Biodegradable polymers have found uses in a wide variety of applications ranging from trash bags that decompose in landfills to implantable medical devices that biodegrade in the body. Most of these applications require that such polymers have adequate physical properties and stability to provide for suitable handling and utility prior to being subjected to end use conditions that promote biodegradation. Further, it is often preferable that these same polymers rapidly or controllably biodegrade once subjected to such end use conditions. In addition, it is often desired that biodegradable polymers used for implantable medical devices be converted under physiological conditions to materials that do not irritate or harm the surrounding tissue. Many biodegradable polymers known in the art lack the combination of physical and/or chemical properties desired to meet the needs for specific applications.

Current and new applications for biodegradable polymers continue to create a need for new polymers that provide some or all of the above-described properties.

BRIEF SUMMARY OF THE INVENTION

Poly(ortho ester) polymers, and methods of making and using poly(ortho ester) polymers are disclosed herein. Poly (ortho ester) polymers as disclosed herein, and compositions including such poly(ortho ester) polymers, can be useful for applications including, for example, medical devices and pharmaceutical compositions. In one embodiment, the poly (ortho ester) polymers disclosed herein are biodegradable.

The presently disclosed poly(ortho ester) polymers (POE) can offer advantages over poly(ortho ester) polymers known in the art. For example, the presently disclosed poly(ortho ester) polymers can hydrolyze at a sufficient rate to be useful for applications that require biodegradable properties, without the necessity of admixing and/or incorporating agents to enhance the hydrolysis rate.

In one aspect, the present disclosure provides a polymer including two or more repeat units selected from a repeat unit of the formula (Formula VI):

$$-[(Z-POE_1)_x-(A-POE_2)_y]-$$

wherein each $POE_1$ and $POE_2$, independently, is represented by the formula:

$$R^{10}(R^9)_2C\underset{O}{\overset{R^{11}}{\diagup}}O\underset{O}{\diagup}\overset{R^{13}}{\diagdown}O\underset{O}{\diagdown}\overset{R^{11}}{\diagup}C(R^9)_2R^{10}\Big]_n$$

or the formula:

$$\Big[O\underset{R^{17}\ H}{\overset{R^{16}O\ \ OR^{15}}{\diagup\diagdown}}(R_{18})_p\underset{H\ R^{17}}{\overset{R^{15}O\ \ OR^{15}}{\diagup\diagdown}}O\Big]$$

wherein:

each $R^9$, $R^{10}$, and $R^{17}$ independently represents hydrogen or an organic group;

each $R^{11}$, $R^{13}$, $R^{15}$, and $R^{16}$ independently represents an organic group;

$R^{18}$ represents oxygen or an organic group and p=0 or 1;

n=0 or 1;

each $R^{11}$ can optionally be joined with $R^{13}$ to form one or more rings;

geminal $R^{15}$ and $R^{16}$ groups can optionally be joined to each other to form rings;

each A, optionally, is $-C(R^1))R^2)-(C(R^5)_2)_r-C(R^3)(R^4)-$, $-Ar^{het}-$, $-Ar^1C(R^6)(R^7)-$, a group of the formula (Formula III) $-Ar^2-C(R^8)_2-Ar^2-(B)_m-$, $-C(=O)-$, $-(C=O)-R-(C=O)-$, or combinations thereof;

R is an organic group;

each $R^1$, $R^2$, $R^3$, $R^4$, and $R^5$ independently represents hydrogen or an organic group, r is 0 to 20, and one or more of $R^1$, $R^2$, $R^3$, $R^4$, and $R^5$ can optionally be joined with one another to form one or more rings;

$Ar^{het}$ represents a 1,2-heteroarylene group;

$Ar^1$ represents a 1,2- or a 1,3-arylene group, or a 1,2- or a 1,3-heteroarylene group, $R^6$ and $R^7$ independently represent hydrogen or an organic group, and $R^6$ and/or $R^7$ can optionally be joined with each other or with the $Ar^1$ group to form one or more rings;

each $Ar^2$ independently represents an arylene group, each $R^8$ independently represents an organic group, B represents an aromatic-containing organic group having a linking oxygen attached to the aromatic ring, and m=0 or 1;

each x is 1 to about 200;

each y is 0 to about 200;

x+y is from 2 to about 400; and each Z is a therapeutic agent containing at least one phenoxy residue and at least one hydroxyl residue or at least a second phenoxy residue.

It should be understood that the "x"s and "y"s can be random and not necessarily in any order. For example, there can be a repeat of several or many "x"s follow by one or more "y"s or vice versa. The resultant polymer can be a random copolymer, a block copolymer or variations thereof.

In one embodiment, the repeat unit only comprises x and y is always 0. That is, the polymer contains only Z in the backbone along with the ortho ester.

In another aspect, the present disclosure provides a method of preparing a polymer. In one embodiment, the method includes: combining components including: at least one hydroxy-containing compound of the formula (Formula I) HO—Z—OH or a mixture of Formula I and Formula (Ia) HO—A—OH; and at least one orthoester of the formula (Formula II)

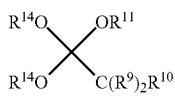

under conditions effective to polymerize at least a portion of the orthoester; and removing byproducts including $R^{14}OH$; wherein each $R^9$ and $R^{10}$ independently represents hydrogen or an organic group; each $R^{11}$ and $R^{14}$ independently represents an organic group; each A is selected from —C($R^1$)($R^2$)—(C($R^5$)$_2$)$_r$—C($R^3$)($R^4$)—, —$Ar^{het}$—, —$Ar^1$C($R^6$)($R^7$)—, a group of the formula (Formula III) —$Ar^2$—C($R^8$)$_2$—$Ar^2$—(B)$_m$—, or combinations thereof; each $R^1$, $R^2$, $R^3$, $R^4$, and $R^5$ independently represents hydrogen or an organic group, r is 0 to 20 (particularly 0 to 15 and more particularly 0 to 10), and one or more of $R^1$, $R^2$, $R^3$, $R^4$, and $R^5$ can optionally be joined with one another to form one or more rings, $Ar^{het}$ represents a 1,2-heteroarylene group; $Ar^1$ represents a 1,2- or a 1,3-arylene group, or a 1,2- or a 1,3-heteroarylene group, $R^6$ and $R^7$ independently represent hydrogen or an organic group, and $R^6$ and/or $R^7$ can optionally be joined with each other or with the $Ar^1$ group to form one or more rings; and each $Ar^2$ independently represents an arylene group, each $R^8$ independently represents an organic group, B represents an aromatic-containing organic group having a linking oxygen attached to the aromatic ring, and m=0 or 1, and Z is a therapeutic agent containing at least one phenoxy residue and at least one hydroxyl residue or at least a second phenoxy residue.

In another aspect, the present disclosure provides another method of preparing a polymer. In one embodiment, the method includes combining components including at least one hydroxy-containing compound of the formula (Formula I) HO—Z—OH or a mixture of Formula I and a compound of the formula (Formula Ia) HO—A—OH and at least one ketene acetal under conditions effective to polymerize at least a portion of the at least one ketene acetal, wherein the at least one ketene acetal is selected from a compound of the formula (Formula IV)

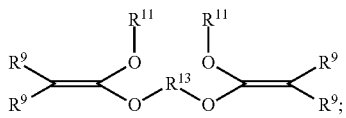

a compound of the formula (Formula V)

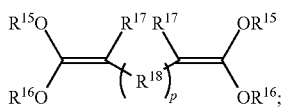

or
combinations thereof; wherein: each $R^9$ and $R^{17}$ independently represents hydrogen or an organic group; each $R^{11}$, $R^{13}$, $R^{15}$, and $R^{16}$ independently represents an organic group; $R^{18}$ represents oxygen or an organic group and p=0 or 1; each $R^{11}$ can optionally be joined with $R^{13}$ to form one or more rings; geminal $R^{15}$ and $R^{16}$ groups can optionally be joined to each other to form rings; each A is selected from —C($R^1$)($R^2$)—(C($R^5$)$_2$)$_r$—C($R^3$)($R^4$)—, —$Ar^{het}$—, —$Ar^1$C($R^6$)($R^7$)—, a group of the formula (Formula III) —$Ar^2$—C($R^8$)$_2$—$Ar^2$—(B)$_m$—, or combinations thereof; each $R^1$, $R^2$, $R^3$, $R^4$, and $R^5$ independently represents hydrogen or an organic group, r is 0 to 20 (particularly 0 to 15 and more particularly 0 to 10), and one or more of $R^1$, $R^2$, $R^3$, $R^4$, and $R^5$ can optionally be joined with one another to form one or more rings, $Ar^{het}$ represents a 1,2-heteroarylene group; $Ar^1$ represents a 1,2- or a 1,3-arylene group, or a 1,2- or a 1,3-heteroarylene group, $R^6$ and $R^7$ independently represent hydrogen or an organic group, and $R^6$ and/or $R^7$ can optionally be joined with each other or with the $Ar^1$ group to form one or more rings; and each $Ar^e$ independently represents an arylene group, each $R^8$ independently represents an organic group, B represents an aromatic-containing organic group having a linking oxygen attached to the aromatic ring, and m=0 or 1, and Z is a therapeutic agent containing at least one phenoxy residue and at least one hydroxyl residue or at least a second phenoxy residue.

In one aspect, each A represents a non-cyclic group —CH($R^1$)—(C($R^3$)$_2$)$_r$—CH($R^2$)—; each $R^1$ and $R^2$ independently represents an organic group; each $R^3$ independently represents hydrogen or an organic group; and r is 0 to 20.

In another aspect, each A represents a cyclic group —C($R^1$)($R^2$)—(C($R^5$)$_2$)$_r$—C($R^3$)($R^4$)—; each $R^1$, $R^2$, $R^3$ and $R^4$, independently represents hydrogen or an organic group, r is 1 to 20 (particularly 1 to 15 and more particularly 1 to 10), and each $R^5$ is an organic group and is joined with the other to form a ring, e.g., trans-1,4-cyclohexanedimethanol.

In another aspect, the present disclosure provides a method of hydrolyzing a poly(ortho ester) polymer. The method includes: providing a poly(ortho ester) polymer that is substantially free of acidic groups, glycolide groups, and lactide groups; exposing the poly(ortho ester) polymer to an aqueous environment; and allowing the poly(ortho ester) polymer to hydrolyze. In an embodiment, the hydrolysis rate and/or drug release rate of the poly(ortho ester) polymer is sufficiently high to allow the poly(ortho ester) polymer to be used in applications requiring biodegradability and/or bioerodibility. Generally, when the poly(ortho ester) polymer is used in an application requiring biodegradability and/or bioerodibility, hydrolyzing the poly(ortho ester) polymer includes forming substantially no acidic byproducts at the hydrolysis site.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The above summary is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

While multiple embodiments are disclosed, still other embodiments of the present invention will become apparent to those skilled in the art from the following detailed description. As will be apparent, the invention is capable of modifications in various obvious aspects, all without departing from

DETAILED DESCRIPTION

Figure 1:
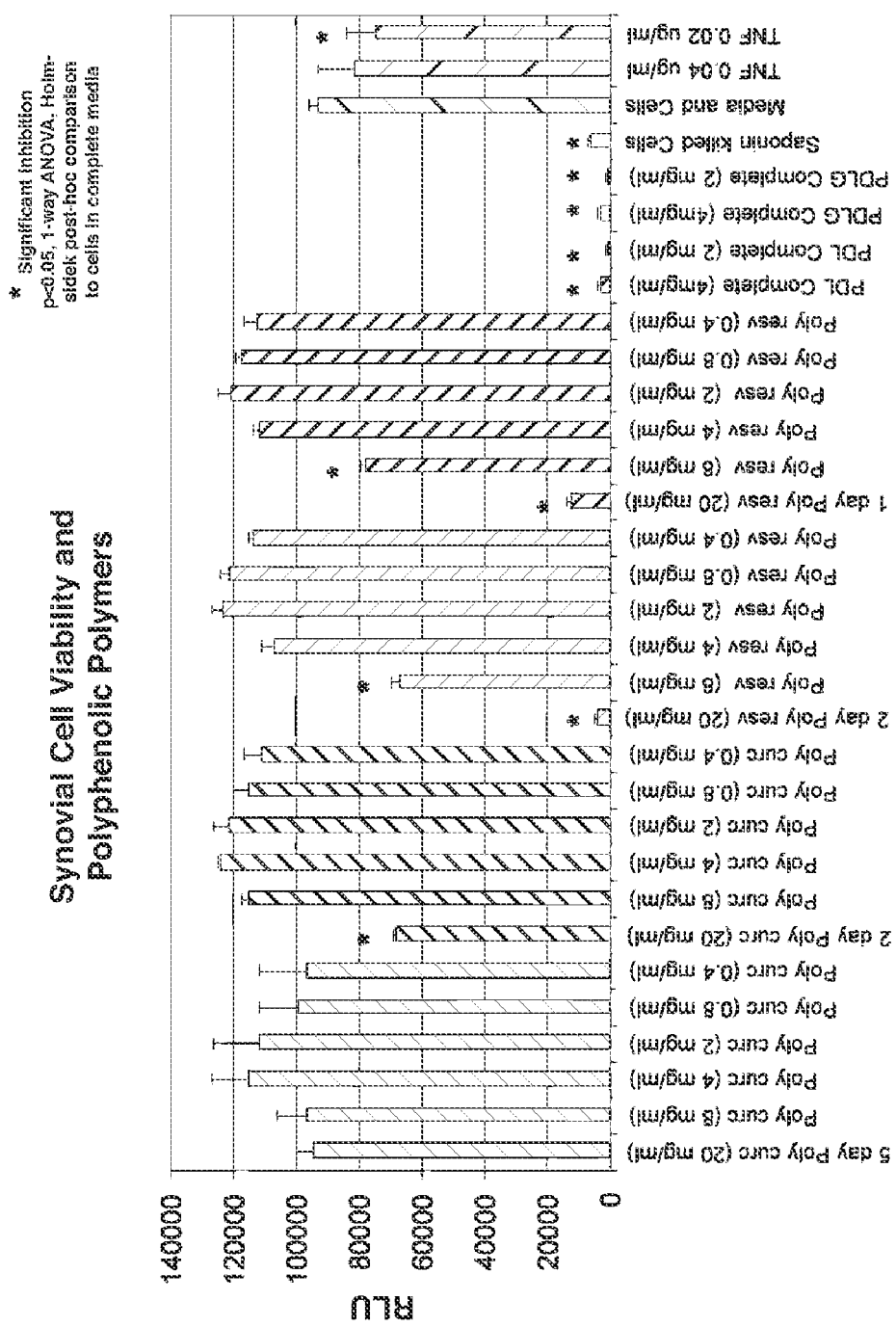
FIG. 1 provides a graphical depiction of the effect of polymer breakdown products on synovial cell viability measured after 24 hours of exposure.
Figure 2:
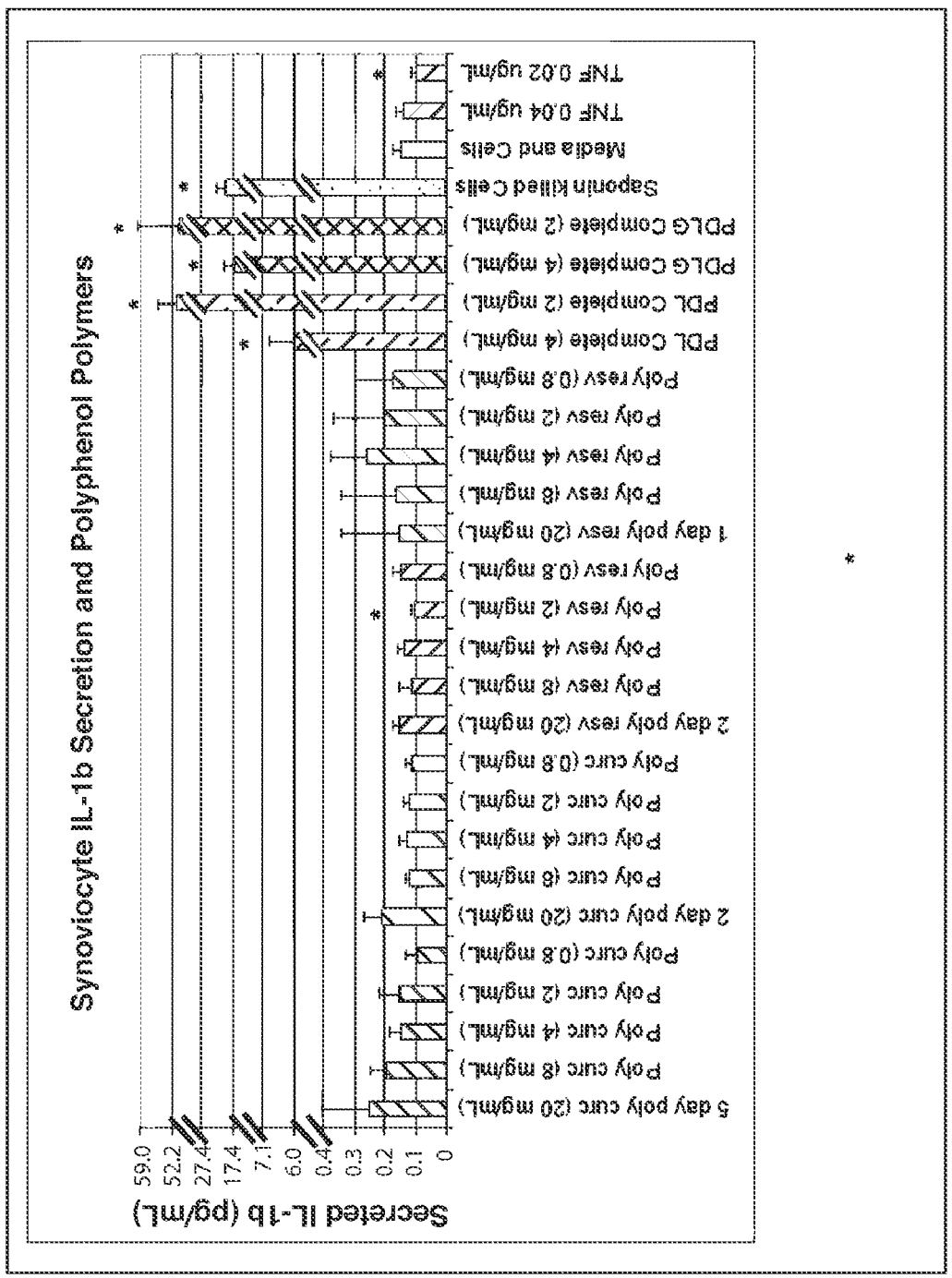
FIG. 2 demonstrates the effect of polymer breakdown products on IL-1b secretion from synoviocytes. * Significantly different p<0.05 Holm-Sidek post-hoc comparison to cells in media.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

A wide variety of biodegradable and/or bioerodible polymers are known in the art. As used herein, "biodegradable" and "bioerodible" are used interchangably and are intended to broadly encompass materials including, for example, those that tend to break down upon exposure to physiological environments. Biodegradable and/or bioerodible polymers known in the art include, for example, linear aliphatic polyester homopolymers (e.g., polyglycolide, polylactide, polycaprolactone, and polyhydroxybutyrate) and copolymers (e.g., poly(glycolide-co-lactide), poly(glycolide-co-caprolactone), poly(glycolide-co-trimethylenecarbonate), poly(lactic acid-co-lysine), poly(lactide-co-urethane), poly(ester-co-amide)); polyanhydrides; and poly(orthoesters). However, many of these polymers lack the combination of physical and/or chemical properties desired for certain applications, particularly in the medical and pharmaceutical fields.

For example, polyglycolide and polylactide homo- and co-polymers are converted under physiological conditions to products including glycolic acid and lactic acid, respectively. For certain medical device applications, the formation of acidic products can limit the utility of such biedegradable polymers. Further, many of the biodegradable polymers noted above biodegrade at a slower rate than desired for specific applications.

Certain poly(orthoesters) are also known to be biodegradable polymers. As used herein, a "poly(ortho ester)" refers to a homo- or co-polymer that includes two or more (i.e., a plurality) of orthoester repeat units. As used herein, an "orthoester" repeat unit is a unit including an orthoester-containing group that is repeated in the polymer at least once. An orthoester group is a group that includes an $RC(OR)_3$ functionality (e.g., an —O—C(R)(OR)—O— or —O—C(OR)$_2$-functionality), with the proviso that R is not oxygen.

The presently disclosed poly(ortho ester) polymers can offer advantages over poly(ortho ester) polymers known in the art. For example, the presently disclosed poly(ortho ester) polymers can hydrolyze at a sufficient rate to be useful for applications that require biodegradable properties, without the necessity of admixing and/or incorporating other agents to enhance the hydrolysis rate. If necessary, a base, such as anhydrous MgO could be used to retard the degradation rate.

The presently disclosed poly(ortho ester) polymers have molecular weights of at least about 10,000, more particularly at least about 20,000 and even more particularly at least about 40,000 g/mol. This is a great improvement over known poly(ortho ester) polymers that typically have molecular weights of 10,000 or less. It is believed that by selection of the appropriate "Z" and "A", as discussed herein, it is possible to obtain the molecular weights. Consequently, the increased molecular weight of the poly(ortho ester) polymer of the invention provide for sustained delivery of the drug (Z) and are biocompatible.

Poly(ortho ester) polymers and convenient methods of preparing such polymers are disclosed herein. Notably the presently disclosed poly(orthoesters) include polymers that are not significantly converted under physiological conditions to acidic products. Further, the present disclosure provides poly(ortho ester) polymers that can biodegrade at a sufficiently high rate to enable them to be considered for use in specific applications.

In one aspect, methods of preparing poly(ortho ester) polymers are disclosed herein. In one embodiment, such methods include combining components including at least one hydroxy-containing compound (a therapeutic agent, "Z", as described herein or a mixture of "Z" and a hydroxy containing compound "A", as described herein) and at least one orthoester, as further described herein below. In another embodiment, such methods include combining components including at least one hydroxy-containing compound, Z, and at least one ketene acetal, as further described herein below.

For some embodiments, suitable hydroxy-containing compounds include compounds of the formula (Formula Ia) HO—A—OH. "A" can be selected from —C($R^1$)($R^2$)—(C($R^5$)$_2$)$_r$—C($R^3$)($R^4$)—, —Ar$^{het}$—, —Ar$^1$C($R^6$)($R^7$)—, a group of the formula (Formula III) —Ar$^2$—C($R^8$)$_2$—Ar$^2$—(B)$_m$—, or combinations thereof. Each $R^1$, $R^2$, $R^3$, $R^4$, and $R^5$ independently represents hydrogen or an organic group, r is 0 to 20 (particularly 0 to 15 and more particularly 0 to 10), and one or more of $R^1$, $R^2$, $R^3$, $R^4$, and $R^5$ can optionally be joined with one another to form one or more rings. $Ar^{het}$ represents a 1,2-heteroarylene group. $Ar^1$ represents a 1,2- or a 1,3-arylene group, or a 1,2- or 1,3-heteroarylene group. $R^6$ and $R^7$ independently represent hydrogen or an organic group, and $R^6$ and/or $R^7$ can optionally be joined with each other or with the $Ar^1$ group to form one or more rings. Each $Ar^2$ independently represents an arylene group, each $R^8$ independently represents an organic group, B represents an aromatic-containing organic group having a linking oxygen attached to the aromatic ring, and m=0 or 1.

A wide variety of hydroxy-containing compounds of the formula (Formula Ia) can be used including, for example, diethyl tartrate, 2-hydroxybenzyl alcohol, 3-hydroxybenzyl alcohol, 2,3-dihydroxypyridine, 4,4'-(1-phenylethylidene)bisphenol, 4,4'-isopropylidenebis(2,6-dimethylphenol), 4,4'-(1,4-phenylenediisopropylidene)bisphenol, and combinations thereof.

For all embodiments, suitable hydroxy-containing compounds include compounds of the formula (Formula I) HO—Z—OH. Z is a therapeutic agent containing at least one phenoxy residue and at least one hydroxyl residue or at least a second phenoxy residue. Alternatively, Z can contain at least two phenoxy residues. It should be understood that more than two phenoxy groups may be present or the combination of phenoxys and hydroxys can equal three or more for a suitable therapeutic agent. Suitable therapeutic agents that have at least one phenoxy group (a phenol) and at least one hyroxyl or at least two phenoxy groups include Apigenin, Astringin, (+)-1-Acetoxypinoresinol, Arzanol, Biochanin A, Campesterol, Catechin, Catechin gallate, Chrysin, Coumestrol, Curcumin, Cyanidin, Daidzein, Daphnetin, Delphinidin, Desoxyrhapontigenin, 7,2'-Dihydroxy-4'-methoxyisoflavanol, Ellagic acid, Epicatechin, Epigallocatechin, Epigallocatechin gallate, Eriodictyol, Fisetin, Gallocatechin, Gallocatechin gallate, Genistein, Gingerol, Glycitein, Helipyrone, Hesperidin, Hespertin, 2'-Hydroxyformoronetin, 2-Hydroxyisoflavanone, Hydroxytyrosol, Isoliquiritigenin, Isorhamnetin, Isorhapontin, Kaempferol, Lariciresinol, Leucopelargonidin, Liquiritigenin, Luteolin, Malvidin, Maringenin, Matairesinol, Methylarzanol, Myricetin, Naringenin, Oleuropein, Oxyresveratrol, Pelargonidin, Peonidin, Petunidin, Piceatannol, Piceid, Pinoresiniol, Pinostilbene, Pinostilbenoside, Proanthocyanidin, Pterostilbene, Punicalagins, Quercetin, Resveratrol, Resveratroloside, Rhaponticin, Rhapontigenin, Rutin, Secoirodoid, Secoisolariciresinol, Silibinin, Silybin, Semimyrtucommulone, Tangeritin, 4,2',4',6'-Tetrahydroxychalcone, Theaflavins, Thearubigin, 4,4',6'-Trihydroxyaurone, Tyrosol, Vanillyl alcohol, (−)-Vestitone, Xanthohumol or combinations thereof.

The term "residue" refers to the material that is devoid of a hydrogen atom. For example, a phenol would be a phenoxide moiety and an alcohol would be a hydroxide or alcoholate.

It should be understood that throughout the application and claims that the poly(ortho ester) polymers disclosed herein, and their methods of preparation, will always contain at least a small percentage of a Z residue in the polymeric backbone. Suitable ranges are from 0.01% to 100% by weight, more particularly, from about 0.1% to about 50%, more particularly from about 1% to about 40% and most particularly from about 5% to about 30% by weight.

As used herein, the term "organic group" is used to mean a hydrocarbon group that is classified as an aliphatic group, cyclic group, or combination of aliphatic and cyclic groups (e.g., alkaryl and aralkyl groups). In the context of the present disclosure, suitable organic groups for polymerization components and polymers disclosed herein are those that do not interfere with the polymerization reactions disclosed herein. In the context of the present disclosure, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tent-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

For some other embodiments, sutiable hydroxy-containing compounds include non-cyclic polyols having no primary hydroxy groups. Such non-cyclic polyols having non primary hydroxy groups include, for example, diols having two secondary hydroxy groups.

Non-cyclic polyols having no primary hydroxy groups can be of the formula HO—CH($R^1$)—(C($R^3$)$_2$)$_r$—CH($R^2$)—OH; wherein: each $R^1$ and $R^2$ independently represents an organic group (e.g., an organic moiety such as methyl); each $R^3$ independently represents hydrogen or an organic group (e.g., an organic moiety); and r is 0 to 20. In certain embodiments each $R^1$ and $R^2$ represents methyl; each $R^3$ represents hydrogen; and r is 0 to 2. Exemplary non-cyclic polyols having no primary hydroxy groups include, but are not limited to, 2,3-butanediol, 2,4-pentanediol, 2,5-hexanediol, and combinations thereof.

In one embodiment, a method of preparing a poly(ortho ester) polymer includes: combining components including: at least one hydroxy-containing compound of the formula (Formula I) HO—Z—OH as described herein above or a mixture of Formula I and a hydroxy-containing compound of the formula (Formula Ia) HO—A—OH as described herein above; and at least one orthoester of the formula (Formula II)

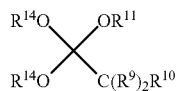

under conditions effective to polymerize at least a portion of the orthoester. The at least one hydroxy-containing compound of the formula (Formula I) HO—Z—OH and the at least one orthoester of the formula (Formula II) can be combined in a ratio selected to provide, for example, oligomers, low molecular weight polymers, and/or high molecular weight polymers. For embodiments in which polymers are desired (e.g., high molecular weight polymers), the at least one hydroxy-containing compound of the formula (Formula I) HO—Z—OH and the at least one orthoester of the formula (Formula II) typically are combined approximately in a 1:1 molar ratio, respectively, although ratios of from 0.9:1 to 1.1:1, respectively can be used in certain embodiments. The method further includes removing byproducts including $R^{14}OH$. Each $R^9$ and $R^{10}$ independently represents hydrogen or an organic group. Each $R^{11}$ and $R^{14}$ independently represents an organic group. The components combined can also include a polymerization agent as described herein below. It should be understood that the compound of the formula (Formula I) can be replaced in part by the compound or compounds of formula (Formula Ia) HO—A—OH in an amount up to about 99% by weight but there must always be a percentage of the compound of formula (Formula I) present in the process and final product.

Optionally, the components can further include, for example, at least one diol different than the at least one hydroxy-containing compound of the formula (Formula I). A wide variety of diols can be used including, for example, diethyleneglycol, triethyleneglycol, tetra(ethyleneglycol), 1,2-propanediol, 1,3-propanediol, 1,4-butanediol, neopentyl glycol, 2,5-hexanediol, 1,6-hexanediol, 1,12-dodecanediol, 1,4-cyclohexanedimethanol, 4-hydroxybenzyl alcohol, 4,4'-biphenol, bis(4-hydroxyphenyl)methane, bisphenol-A, hydroquinone, 1,4-benzenedimethanol, 2-methoxyhydroquinone, 2,3-dimethylhydroquinone, and combinations thereof.

In another embodiment, a method of preparing a poly (ortho ester) polymer includes: combining components including: at least one non-cyclic polyol having no primary hydroxy groups as described herein above; at least one compound of the formula (Formula I), and at least one orthoester of the formula (Formula II)

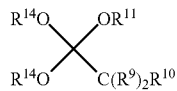

under conditions effective to polymerize at least a portion of the orthoester. The at least one non-cyclic polyol having no primary hydroxy groups and the at least one orthoester of the formula (Formula II) can be combined in a ratio selected to provide, for example, oligomers, low molecular weight polymers, and/or high molecular weight polymers. For embodiments in which polymers are desired (e.g., high molecular weight polymers), the at least one non-cyclic polyol having no primary hydroxy groups and the at least one orthoester of the formula (Formula II) typically are combined approximately in a 1:1 molar ratio, respectively, although ratios of from 0.9:1 to 1.1:1, respectively can be used in certain embodiments. The method further includes removing byproducts including $R^{14}OH$. Each $R^9$ and $R^{10}$ independently represents hydrogen or an organic group. Each $R^{11}$ and $R^{14}$ independently represents an organic group. The components combined can also include a polymerization agent as described herein below. Again, it should be understood that the compound(s) of the formula (Formula Ia) can be replaced in part by the compound of formula (Formula I) HO—Z—OH in an amount up to about 99% by weight at there must always be a percentage of the compound of formula (Formula I) present in the process and final product.

Optionally, the components can further include, for example, at least one diol different than the at least one non-cyclic polyol having no primary hydroxy groups. A wide variety of diols can be used including, for example, ethyleneglycol, diethyleneglycol, triethyleneglycol, tetra(ethyleneglycol), 1,3-propanediol, 1,4-butanediol, neopentyl glycol, 1,6-hexanediol, 1,12-dodecanediol, 1,4-cyclohexanedimethanol, 4-hydroxybenzyl alcohol, 4,4'-biphenol, bis(4-hydroxyphenyl)methane, bisphenol-A, hydroquinone, 1,4-benzenedimethanol, 2-methoxyhydroquinone, 2,3-dimethylhydroquinone, and combinations thereof.

For at least some of the above-described embodiments, conditions effective to polymerize include combining at least a portion of the components without adding a solvent. In other embodiments, conditions effective to polymerize further include combining a solvent, preferably a dry organic solvent. In certain embodiments, the solvent preferably forms an azeotrope with $R^{14}OH$. Suitable solvents include, for example, tetrahydrofuran, dioxane, toluene, methylene chloride, chloroform, N-methylpyrrolidone, N,N-dimethylacetamide, N,N-dimethylformamide, and combinations thereof. In certain embodiments, at least a portion of the components are combined under an inert atmosphere.

Byproducts of the reaction including, for example, $R^{14}OH$, can be removed, for example, by application of heat and/or vacuum to the reaction mixture. When a solvent is added, a convenient method of removing such byproducts includes distilling the byproducts under azeotropic conditions.

Optionally, combining components can further include combining an additional polymerizable compound. A wide variety of additional polymerizable compounds can be used including, for example, ketene acetals, monofunctional orthoesters, polyfunctional orthoesters, imagable compounds, compounds having latent reactive sites, and combinations thereof. The additional polymerizable compound can also be an orthoester different than the at least one orthoester described herein above.

In another embodiment, a method of preparing a poly (ortho ester) polymer includes: combining components including at least one hydroxy-containing compound of the formula (Formula I) HO—Z—OH or a mixture of the compound of the formula (Formula I) and at least one hydroxy-containing compound of the formula (Formula Ia) HO—A—OH as described herein above and at least one ketene acetal under conditions effective to polymerize at least a portion of the at least one ketene acetal. The at least one ketene acetal is selected from a compound of the formula (Formula IV)

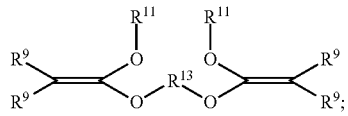

a compound of the formula (Formula V)

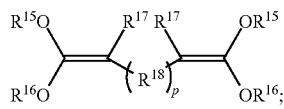

or combinations thereof. Each $R^9$ and $R^{17}$ independently represents hydrogen or an organic group. Each $R^{11}$, $R^{13}$, $R^{15}$, and $R^{16}$ independently represents an organic group. $R^{18}$ represents oxygen or an organic group and p=0 or 1. Each $R^{11}$ can optionally be joined with $R^{13}$ to form one or more rings, and geminal $R^{15}$ and $R^{16}$ groups can optionally be joined to each other to form rings. The at least one ketene acetal of Formula IV and/or Formula V have a purity of at least 98 wt-%, more particulary at least 99 wt-%, and most particularly at least 99.5 wt-% as measured using the procedure of Pogany et al., J. of Chromatography, 508:179-186 (1990). Ketene acetals can be prepared by methods known in the art including for example, those described in Crivello et al., J. of Polymer Science, 34:3091-3102 (1996); Ng et al., Macromolecular Syntheses, 11:23-26 (1992); and U.S. Pat. Nos. 4,513,143 (Ng et al.) and 4,532,335 (Helwing). The at least one hydroxy-containing compound of the formula (Formula I) or the mixture of Formula I and Formula Ia and the at least one ketene acetal of Formula IV and/or Formula V can be combined in a ratio selected to provide, for example, oligomers, low molecular weight polymers, and/or high molecular weight polymers. For embodiments in which polymers are desired (e.g., high molecular weight polymers), the at least one hydroxy-containing compound of the formula (Formula I) and the at least one ketene acetal of Formula IV and/or Formula V typically are combined approximately in a molar ratio of 1:1, respectively. In certain embodiments, the at least one hydroxy-containing compound of the formula (Formula I) and the at least one ketene acetal of Formula IV and/or Formula V are combined in a molar ratio such that the at least one ketene acetal of Formula IV and/or Formula V is present in a slight molar excess. For example, in certain embodiments, the at least one hydroxy-containing compound of the formula (Formula I) and the at least one ketene acetal of Formula IV and/or Formula V are combined in a molar ratio of 1 to at least 1.001, particularly in a molar ratio of 1 to at least 1.01, and more particularly in a molar ratio of 1 to at least 1.02. in certain embodiments, the at least one hydroxy-containing compound of the formula (Formula I) and the at least one ketene acetal of Formula IV and/or Formula V are combined in a molar ratio of 1 to at most 1.1, particularly in a molar ratio of 1 to at most 1.05, and more particularly in a molar ratio of 1 to at most 1.03.

The components combined can also include a polymerization agent as described herein below.

In certain embodiments, the compound of the formula (Formula IV) is represented by Formula IV(a):

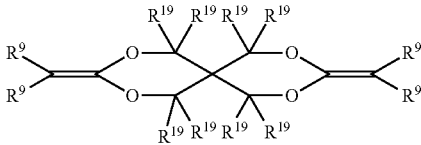

wherein each $R^9$ and $R^{19}$, independently represents hydrogen or an organic group. In certain embodiments, each $R^9$ and $R^{19}$ represents hydrogen.

Optionally, the components can further include, for example, at least one diol different than the at least one hydroxy-containing compound of the formula (Formula Ia). A wide variety of diols can be used including, for example, ethyleneglycol, diethyleneglycol, triethyleneglycol, tetra (ethyleneglycol), 1,3-propanediol, 1,4-butanediol, neopentyl glycol, 2,5-hexanediol, 1,6-hexanediol, 1,12-dodecanediol, 1,4-cyclohexanedimethanol, 4-hydroxybenzyl alcohol, 4,4'-biphenol, bis(4-hydroxyphenyl)methane, bisphenol-A, hydroquinone, 1,4-benzenedimethanol, 2-methoxyhydroquinone, 2,3-dimethylhydroquinone, and combinations thereof.

In another embodiment, a method of preparing a poly (ortho ester) polymer includes: combining components including at least one non-cyclic polyol having no primary hydroxy groups as described herein above and at least one ketene acetal under conditions effective to polymerize at least a portion of the at least one ketene acetal. The at least one ketene acetal is selected from a compound of the formula (Formula IV)

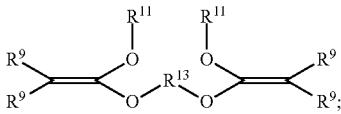

a compound of the formula (Formula V)

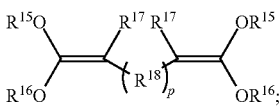

or combinations thereof. Each $R^9$ and $R^{17}$ independently represents hydrogen or an organic group. Each $R^{11}$, $R^{13}$, $R^{15}$, and $R^{16}$ independently represents an organic group. $R^{18}$ represents oxygen or an organic group and p=0 or 1. Each $R^{11}$ can optionally be joined with $R^{13}$ to form one or more rings, and geminal $R^{15}$ and $R^{16}$ groups can optionally be joined to each other to form rings. The at least one ketene acetal of Formula IV and/or Formula V have a purity of at least 98 wt-%, more particularly at least 99 wt-%, and most particularly at least 99.5 wt-% as measured using the procedure of Pogany et al., J. of Chromatography, 508:179-186 (1990). Ketene acetals can be prepared by methods known in the art including for example, those described in Crivello et al., J. of Polymer Science, 34:3091-3102 (1996); Ng et al., Macromolecular Syntheses, 11:23-26 (1992); and U.S. Pat. Nos. 4,513,143 (Ng et al.) and 4,532,335 (Helwing). The at least one non-cyclic polyol having no primary hydroxy groups and the at least one ketene acetal of Formula IV and/or Formula V can be combined in a ratio selected to provide, for example, oligomers, low molecular weight polymers, and/or high molecular weight polymers. For embodiments in which polymers are desired (e.g., high molecular weight polymers), the at least one non-cyclic polyol having no primary hydroxy groups and the at least one ketene acetal of Formula IV and/or Formula V typically are combined approximately in a molar ratio of 1:1, respectively. In certain embodiments, the at least one non-cyclic polyol having no primary hydroxy groups and the at least one ketene acetal of Formula IV and/or Formula V are combined in a molar ratio such that the at least one ketene acetal of Formula IV and/or Formula V is present in a slight molar excess. For example, in certain embodiments, the at least one non-cyclic polyol having no primary hydroxy groups and the at least one ketene acetal of Formula IV and/or Formula V are combined in a molar ratio of 1 to at least 1.001, particularly in a molar ratio of 1 to at least 1.01, and more particularly in a molar ratio of 1 to at least 1.02. in certain embodiments, the at least one non-cyclic polyol having no primary hydroxy groups and the at least one ketene acetal of Formula IV and/or Formula V are combined in a molar ratio of 1 to at most 1.1, particularly in a molar ratio of 1 to at most 1.05, and more particularly in a molar ratio of 1 to at most 1.03.

The components combined can also include a polymerization agent as described herein below.

In certain embodiments, the compound of the formula (Formula IV) is represented by Formula IV(a):

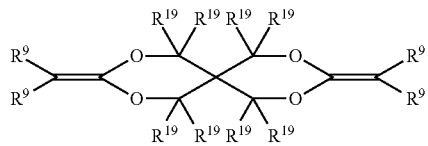

wherein each $R^9$ and $R^{19}$, independently represents hydrogen or an organic group. In certain embodiments, each $R^9$ and $R^{19}$ represents hydrogen.

Optionally, the components can further include, for example, at least one diol different than the at least one non-cyclic polyol having no primary hydroxy groups. A wide variety of diols can be used including, for example, ethyleneglycol, diethyleneglycol, triethyleneglycol, tetra(ethyleneglycol), 1,3-propanediol, 1,4-butanediol, neopentyl glycol, 1,6-hexanediol, 1,12-dodecanediol, 1,4-cyclohexanedimethanol, 4-hydroxybenzyl alcohol, 4,4'-biphenol, bis(4-hydroxyphenyl)methane, bisphenol-A, hydroquinone, 1,4-benzenedimethanol, 2-methoxyhydroquinone, 2,3-dimethylhydroquinone, and combinations thereof.

For at least some of the above-described embodiments, optionally, the components can further include, for example, at least one mono-hydroxy-containing compound. A wide variety of mono-hydroxy-containing compounds can be used including, for example, methanol, ethanol, propanol, butanol, pentanol, hexanol, decanol, dodecanol, 2-methoxyethanol, 2-ethyoxyethanol, di(ethyleneglycol) monomethyl ether, di(ethyleneglycol) monoethyl ether, tri(ethyleneglycol) monomethyl ether, tri(ethyleneglycol) monoethyl ether, tetra(ethyleneglycol) monomethyl ether, tetra(ethyleneglycol) monoethyl ether, and combinations thereof.

In some embodiments, conditions effective to polymerize include combining at least a portion of the components without adding a solvent. In other embodiments, conditions effective to polymerize further include combining a solvent, particularly a dry organic solvent. Suitable solvents include, for example, tetrahydrofuran, dioxane, toluene, methylene chloride, chloroform, N-methylpyrrolidone, N,N-dimethylacetamide, N,N-dimethylformamide, and combinations thereof. When a solvent is used, components are typically combined to give at least 1% by weight solids, preferably at least 5% by weight solids, and more preferably at least 10% by weight solids. When a solvent is used, components are typically combined to give at most 70% by weight solids, preferably at most 60% by weight solids, and more preferably at most 50% by weight solids. In certain embodiments, at least a portion of the components are combined under an inert atmosphere.

Optionally, combining components can further include combining an additional polymerizable compound. A wide variety of additional polymerizable compounds can be used including, for example, orthoesters, monofunctional ketene acetals, polyfunctional ketene acetals, imagable compounds, compounds having latent reactive sites, and combinations thereof. The additional polymerizable compound can also be a ketene acetal different than the at least one ketene acetal described herein above.

A polymerization agent can be used to initiate and/or propagate the polymerization reactions described herein above. A wide variety of polymerization agents can be used that are known in the art to catalyze addition polymerizations. Typically, the polymerization agent provides for polymerization through a cationic, an anionic, a free radical, and/or an organometallic pathway. The polymerization agent may be present in catalytic amounts, or alternatively, may be used in stoichiometric amounts with partial or total consumption of the polymerization agent during the polymerization reaction.

In some embodiments, the polymerization agent includes a Lewis acid or a Brønsted-Lowry acid. Suitable Lewis acids typically include one or more elements such as Al, Fe, B, Zn, Sb, Ti, Cu, Sn, Si, and the like. Examples of suitable Lewis acids include, for example, boron trifluoride and/or boron trifluoride etherate, zinc chloride, zinc iodide, zinc triflate, antimony pentachloride, and the like, and combinations thereof.

Suitable Brønsted-Lowry acids include, for example, hydrochloric acid, p-toluenesulfonic acid, methanesulfonic acid, trifluoromethanesulfonic acid, camphorsulfonic acid, and the like.

The ratio of the polymerization agent to the other components can be varied as desired, and is typically selected to provide the desired reaction time at the selected reaction temperature for the specific polymerization agent. The ratio of the polymerization agent to the other components can also be varied to influence the molecular weight of the resulting polymers, with lower ratios typically resulting in higher molecular weights. In some embodiments, at least 0.0000001 mole %, sometimes at least 0.000001 mole %, and other times at least 0.00001 mole % of polymerization agent is used, based on the total moles of hydroxy-containing compound and polymerization agents. In some embodiments, at most 30 mole %, sometimes at most 20 mole %, and other times at most 10 mole % of polymerization agent is used, based on the total moles of hydroxy-containing compound and polymerization agents. In certain embodiments, a solution of a Brønsted-Lowry acid (e.g., 1% by weight p-toluenesulfonic acid) in a solvent (tetrahydrofuran) can be used as a polymerization agent.

Suitable polymerization agents may be monofunctional (i.e., having one initiation site), difunctional (i.e., having two initiation sites), or polyfunctional (i.e., having more than two initiation sites). For cases in which the polymerization agent is incorporated into the polymer chain, polyfunctional polymerization agents can lead to highly branched polymer structures (e.g., star structures).

In certain embodiments, components including the at least one hydroxy-containing compound and the polymerization agent can be combined neat (e.g., without adding a solvent). In other certain embodiments, components including the at least one hydroxy-containing compound and the polymerization agent can be combined in a dry organic solvent at a concentration selected to provide a convenient reaction rate. Typically, rapid addition of the polymerization agent to the other components (e.g., addition over at most 60 seconds, and sometimes at most 1 second) can be used for producing higher molecular weight poly(ortho ester) polymers. See, for example, Ng et al., *J. of Controlled Release*, 65:367-374 (2000). Typically and preferably, at least a portion of the components are combined under an inert atmosphere. The reaction temperature can be selected and/or varied as desired to provide a convenient reaction rate.

The polymerization methods disclosed herein can provide poly(ortho ester) polymers. In certain embodiments, the present disclosure provides a polymer including two or more repeat units selected from a repeat unit of the formula (Formula VI):

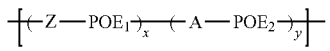

wherein each $POE_1$ and $POE_2$, independently, is represented by the formula:

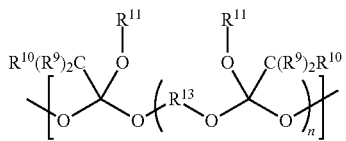

or the formula:

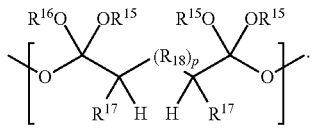

Each $R^9$, $R^{10}$, and $R^{17}$ independently represents hydrogen or an organic group. Each $R^{11}$, $R^{13}$, $R^{15}$, and $R^{16}$ independently represents an organic group; $R^{18}$ represents oxygen or an organic group and p=0 or 1, and n=0 or 1. Each $R^{11}$ can optionally be joined with $R^{13}$ to form one or more rings, and geminal $R^{15}$ and $R^{16}$ groups can optionally be joined to each other to form rings. Z is as defined above.

In some embodiments, each A is as defined herein above for hydroxy-containing compounds of the formula (Formula Ia) HO—A—OH.

In some other embodiments, each A represents the non-cyclic group —CH($R^1$)—(C($R^3$)$_2$)$_r$—CH($R^2$)—; each $R^1$ and $R^2$ independently represents an organic group (e.g., an organic moiety); each $R^3$ independently represents hydrogen or an organic group (e.g., an organic moiety); and r is 0 to 20. In certain embodiments, each $R^1$ and $R^2$ represents methyl; each $R^3$ represents hydrogen; and r is 0 to 2.

In another aspect, each A represents a cyclic group —C($R^1$)($R^2$)—(C($R^5$)$_2$)$_r$—C($R^3$)($R^4$)—; each $R^1$, $R^2$, $R^3$ and $R^4$, independently represents hydrogen or an organic group, r is 1 to 20 (particularly 1 to 15 and more particularly 1 to 10), and each $R^5$ is an organic group and is joined with the other to form a ring, e.g., trans-1,4-cyclohexanedimethanol.

In certain embodiments, the POE repeat units of the formula (Formula VI) is represented by Formula VIa:

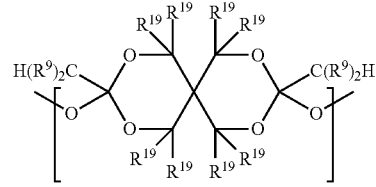

wherein each $R^9$ and $R^{19}$ independently represents hydrogen or an organic group.

In certain embodiments, each $R^{19}$ represents hydrogen and each $R^9$ independently represents hydrogen or methyl.

In some embodiments, each A is as defined herein above for hydroxy-containing compounds of the formula (Formula Ia) HO—A—OH.

In some other embodiments, each A represents the non-cyclic group —CH($R^1$)—(C($R^3$)$_2$)$_r$—CH($R^2$)—; each $R^1$ and $R^2$ independently represents an organic group (e.g., an organic moiety); each $R^3$ independently represents hydrogen or an organic group (e.g., an organic moiety); and r is 0 to 20. In certain embodiments, each $R^1$ and $R^2$ represents methyl; each $R^3$ represents hydrogen; and r is 0 to 2.

In another aspect, each A represents a cyclic group —C($R^1$)($R^2$)—(C($R^5$)$_2$)$_r$—C($R^3$)($R^4$)—; each $R^1$, $R^2$, $R^3$ and $R^4$, independently represents hydrogen or an organic group, r is 1 to 20 (particularly 1 to 15 and more particularly 1 to 10), and each $R^5$ is an organic group and is joined with the other to form a ring, e.g., trans-1,4-cyclohexanedimethanol.

In the above-disclosed polymers, any of the R substituents that are "organic groups" can include as at least a portion thereof, for example, an orthoester functionality (e.g., at least a portion of Formula II, Formula VI, or Formula VII); a ketene acetal functionality (e.g., at least a portion of Formula IV or Formula V); an imagable functionality (e.g., one or more of a radiopaque functionality such as an iodinated group, a ferromagnetic functionality, and a magnetic susceptible functionality such as Fe, Cr, Ni, and Gd); a latent reactive functionality (e.g., ethylenic unsaturation and/or oxygen-containing rings suitable for latent crosslinking after polymerization); or combinations thereof.

The polymers disclosed herein can include a single orthoester-containing repeat unit (i.e., a homopolymer), or two or more different repeat units (i.e., a copolymer). In such copolymers, the two or more different repeat units can all be different orthoester-containing repeat units of Formula VI and/or Formula VII, or alternatively, one or more orthoester-containing repeat units of Formula VI and/or Formula VII in combination with one or more repeat units that are not of Formula VI or Formula VII (e.g., repeat units that include, for example, ether groups, acetal groups, and/or ketal groups). The polymers disclosed herein can be linear polymers, crosslinkable polymers, and/or crosslinked polymers.

Copolymers as disclosed herein can be random copolymers, alternating copolymers, block copolymers, graft copolymers, or combinations thereof. For example, mixtures of components can be combined with a polymerization agent to prepare random and/or alternating copolymers. For another example, one or more components can be combined with a polymerization agent and allowed to react until all the components are consumed, followed by the addition of one or more different components, and optionally additional polymerization agent (which can be the same or different than the first optional polymerization agent, if present), which are then allowed to react to prepare block and/or graft copolymers.

Block copolymers in which at least one block of the block copolymer is a poly(ortho ester) block including two or more repeat units selected from the group consisting of repeat units of Formula VI, repeat units of Formula VII, and combinations thereof, can be of particular interest for certain applications. The at least one other block of such block copolymers can be selected from blocks having a wide variety of repeat units including, for example, alpha-hydroxy alkanoates, beta-hydroxy alkanoates, gamma-hydroxy alkanoates, delta-hydroxy alkanoates, epsilon-hydroxy alkanoates, gylcols, carbonates, acetals, urethane-containing groups, carbamate-containing groups, or combinations thereof. In certain embodiments, the at least one other block of such block copolymers can be a polyketal block. In other certain embodiments, the at least one other block of such block copolymers can be a poly(alkyleneglycol) block including alkylene glycol repeat units.

Optionally, the poly(ortho ester) polymer can be further reacted as a soft segment of a segmented polymer. Exemplary segmented polymers include, for example, polyurethanes, polyethylenes, polycarbonates, polyureas, and combinations thereof. In some embodiments, copolymers can be formed by starting with an oligomeric or polymeric macromolecule (e.g., polyethylene glycol) and forming poly(ortho ester) blocks thereon by the polymerization of the components described herein. In other embodiments, copolymers can be formed by starting with a poly(ortho ester) polymer and reacting the poly(ortho ester) polymer with additional components (e.g., monomers, oligomers, polymers, and/or other reactive compounds).

Typically and preferably, the poly(ortho ester) polymers disclosed herein are biodegradable. Typically, the average molecular weight (and preferably the weight average molecular weight) of the polymers disclosed herein is at least 20,000 Daltons, and sometimes at least 50,000 Daltons, 60,000 Daltons, or even 100,000 Daltons or more. Typically the polydispersity index (PDI) of the polymers disclosed herein is at most 5, and sometimes at most 3, and other times at most 2.

In another aspect, a poly(ortho ester) polymer that is substantially free of acidic groups, glycolide groups, and lactide groups is disclosed. Preferably, the hydrolysis rate and/or drug release rate of the poly(ortho ester) polymer is sufficiently high to allow the poly(ortho ester) polymer to be used in applications requiring biodegradability and/or bioerodibility.

In another aspect, a poly(ortho ester) polymer having a glass transition temperature ($T_g$) of at least 50° C. is disclosed. Preferably, the hydrolysis rate and/or drug release rate of the poly(ortho ester) polymer is sufficiently high to allow the poly(ortho ester) polymer to be used in applications requiring biodegradability and/or bioerodibility.

While there are a number of different approaches to synthesizing ortho esters, one convenient approach is to react, for example, resveratrol with a bis(ketene acetal) such as Detosu, as shown in Scheme 1. The degree of crosslinking in the polymer thus formed can be controlled by the stoichiometry of the starting materials. In the upper product, more than one equivalent of Detosu has been used, resulting in a relatively crosslinked system. In the lower product, equimolar ratios of the starting materials are assumed. While the lower product is depicted as a perfectly linear polymer, it is to be understood that there will be some degree of crosslinking and/or branching, along with a corresponding number of free phenol groups.

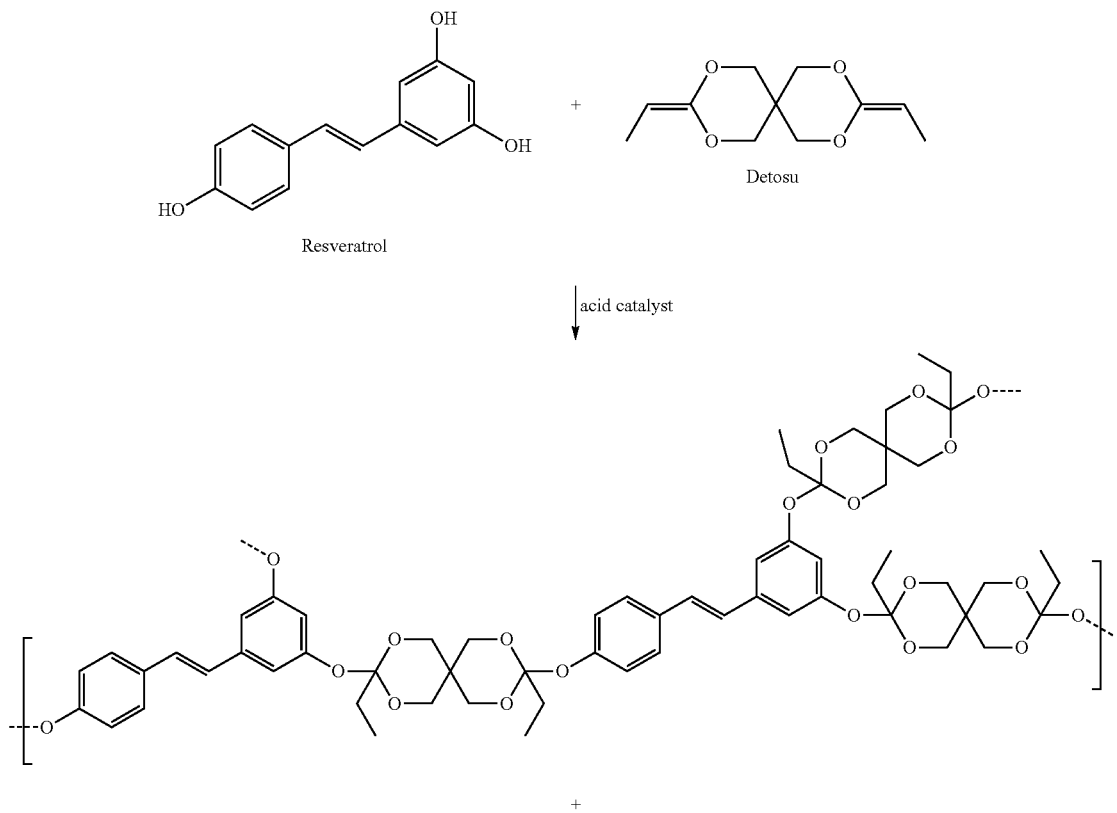

Scheme 1

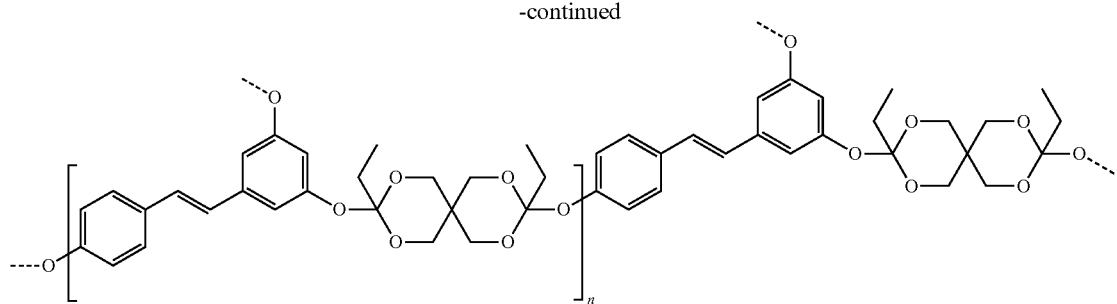

Copolyorthoesters based on resveratrol can also synthesized by using additional diols, as shown in Scheme 2. In this case, 1,6-hexanediol is used. By the selection of diols used as comonomers with resveratrol and by controlling the degree of crosslinking by the ratio of diols to Detosu, copolymers with a wide range of physical properties, degradation rates, and resveratrol release rates are accessible.

poly(ortho ester) polymer is used in an application requiring biodegradability and/or bioerodibility, hydrolyzing the poly (ortho ester) polymer includes forming substantially no acidic byproducts at the hydrolysis site.

For certain applications, a poly(ortho ester) polymer as disclosed herein can be blended with another polymer (e.g., the same or different than the poly(ortho ester) polymers

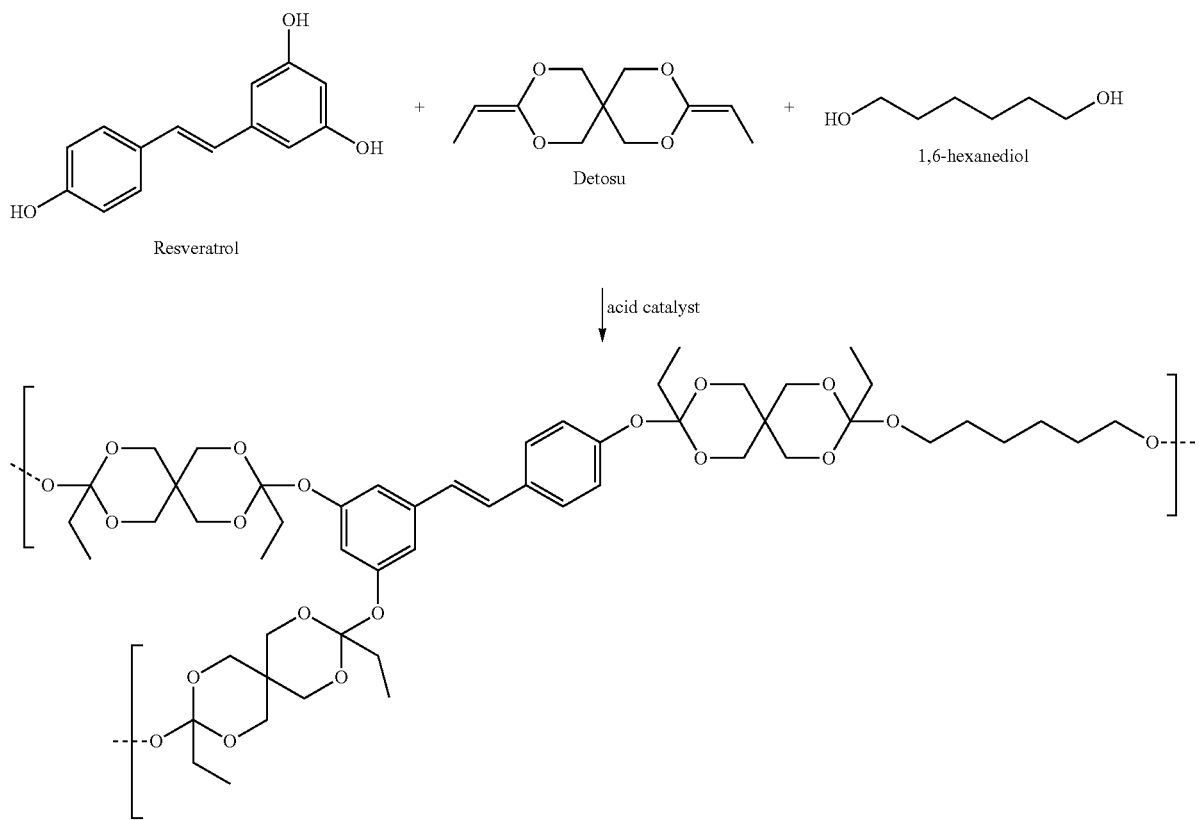

In another aspect, a method of hydrolyzing a poly(ortho ester) polymer is provided. The method includes: providing a poly(ortho ester) polymer that is substantially free of acidic groups, glycolide groups, and lactide groups; exposing the poly(ortho ester) polymer to an aqueous environment; and allowing the poly(ortho ester) polymer to hydrolyze. Preferably, the hydrolysis rate and/or drug release rate of the poly (ortho ester) polymer is sufficiently high to allow the poly (ortho ester) polymer to be used in applications requiring biodegradability and/or bioerodibility. Preferably, when the disclosed herein) to provide the desired physical and/or chemical properties. For example, two poly(ortho ester) polymers having different molecular weights can be blended to optimize the release rate of a biologically active agent. For another example, two poly(ortho ester) polymers having different repeat units can be blended to provide desired physical and/or chemical properties. For even another example, a poly (ortho ester) polymer can be blended with another polymer that is not a poly(ortho ester) polymer to provide desired physical and/or chemical properties.

Poly(ortho ester) polymers as disclosed herein can be used in various combinations for various applications. They can be used as tissue-bulking agents in urological applications for bulking the urinary sphincter to prevent stress incontinence or in gastrological applications for bulking of the lower esophageal sphincter to prevent gastroesophageal reflux disease. They can be used for replacements for nucleus pulposis or repair of annulus in intervertebral disc repair procedures. They can be used as surgical void fillers, for example, in reconstructive or cosmetic surgery (e.g., for filling a void after tumor removal). They can be used to repair aneurysms, hemorrhagic stroke or other conditions precipitated by failure of a blood vessel. They can be used to prevent surgical adhesions. They can be used for local pain relief when administered in a depot to treat post operative pain or sciatica. They can be used to treat systemic pain or chronic pelvic pain when administered intraspinally, specifically epidurally. Poly(ortho ester) polymers as disclosed herein can further be used for applications such as scaffolds or supports for the development and/or growth of cells for applications including, for example, tissue engineering and the fabrication of artificial organs.

Poly(ortho ester) polymers as disclosed herein can be used in injectable compositions. Such injectable compositions could be used as tissue bulking agents (e.g., for the treatment of urinary stress incontinence, for the treatment of gastroesophageal reflux disease, or serving to augment a degenerated intervertebral disc), void fillers (e.g., in cosmetic or reconstructive surgery, such as serving as a replacement for the nucleus pulposis), or as an injectable drug delivery matrix.

In some embodiments, no additives would be needed. In some embodiments, one or more polymers can be combined with a solvent such as N-methyl-2-pyrrolidone or dimethylsulfoxide (DMSO), which are fairly biocompatible solvents. The solvent can diffuse away after injection and the polymer can remain in place. Such materials can be administered to a desired site (e.g., a surgical site) using a syringe, catheter, other medical device or by hand.

Also, injectable compositions could include crosslinkers (such as diacrylates), plasticizers (such as triethyl citrate), lipids (soybean oil), poly(ethylene glycol) (including those with the ends blocked with methyls or similar groups), silicone oil, partially or fully fluorinated hydrocarbons, N-methyl-2-pyrrolidone, or mixtures thereof.

Polymers disclosed herein can be used in combination with a variety of particulate materials. For example, they can be used with moisture curing ceramic materials (e.g., tricalcium phosphate) for vertebroplasty cements, bone void filling (due to disease such as cancer or due to fracture). They can be used in combination with inorganic materials such as hydroxylapatite to form pastes for use in bone healing, sealing, filling, repair, and replacement. They can be used as or in combination with polymer microspheres that can be reservoirs for a biologically active agent such as a protein, DNA plasmid, RNA plasmid, antisense agent, etc.

Alternatively, poly(orthoesters) as disclosed herein can be used in combination with other materials to form a composite (e.g., a polymer having an additive therein). In addition to one or more poly(ortho ester) polymers, composites can include a wide variety of additives, and particularly particulate additives, such as, for example, fillers (e.g., including particulate, fiber, and/or platelet material), other polymers (e.g., polymer particulate materials such as polytetrafluoroethylene can result in higher modulus composites), imaging particulate materials (e.g., barium sulfate for visualizing material placement using, for example, fluoroscopy), biologically derived materials (e.g., bone particles, cartilage, demineralized bone matrix, platelet gel, and combinations thereof), and combinations thereof. Additives can be dissolved, suspended, and/or dispersed within the composite. For particulate additives, the additive is typically dispersed within the composite.

Poly(ortho ester) polymers as described herein can be combined with fibers, woven or nonwoven fabric for reconstructive surgery, such as the in situ formation of a bone plate or a bone prosthesis.

In certain embodiments, one or more poly(ortho ester) polymers as disclosed herein can be shaped to form a medical device, preferably a biodegradable medical device. Shapes can be in the form of a depot, rod, noodle, microsphere, macrosphere, gel, strip, ribbon, or any other imaginable form. The one or more polymers can be shaped by methods known in the art including compression molding, injection molding, casting, extruding, milling, blow molding, spray drying or combinations thereof. As used herein, a "medical device" includes devices that have surfaces that contact tissue, bone, blood, or other bodily fluids in the course of their operation, which fluids are subsequently used in patients. This can include, for example, extracorporeal devices for use in surgery such as blood oxygenators, blood pumps, blood sensors, tubing used to carry blood, and the like which contact blood which is then returned to the patient. This can also include endoprostheses implanted in blood contact in a human or animal body such as vascular grafts, stents, pacemaker leads, heart valves, and the like, that are implanted in blood vessels or in the heart. This can also include devices for temporary intravascular use such as catheters, guide wires, and the like which are placed into the blood vessels or the heart for purposes of monitoring or repair. A medical device can also be fabricated by polymerizing components including at least one hydroxy-containing compound and compounds of Formula II, Formula IV, and/or Formula V in a suitable mold.

Poly(ortho ester) polymers as disclosed herein can also be coated onto a substrate if desired. A coating mixture of the polymer can be prepared using solvents such as toluene, chloroform, tetrahydrofuran, perfluorinated solvents, and combinations thereof. Preferred solvents include those that can be rendered moisture-free and/or those that have no active hydrogens. The coating mixture can be applied to an appropriate substrate such as uncoated or polymer coated medical wires, catheters, stents, prostheses, penile inserts, and the like, by conventional coating application methods. Such methods include, but are not limited to, dipping, extruding, spraying, wiping, painting, solvent swelling, molding and the like. After applying the coating solution to a substrate, the solvent is preferably allowed to evaporate from the coated substrate.

The materials of a suitable substrate include, but are not limited to, polymers, metal, glass, ceramics, composites, and multilayer laminates of these materials. The coating may be applied to metal substrates such as the stainless steel used for guide wires, stents, catheters and other devices. Organic substrates that may be coated with polymers as disclosed herein include, but are not limited to, polyether-polyamide block copolymers, polyethylene terephthalate, polyetherurethane, polyesterurethane, other polyurethanes, silicone, natural rubber, rubber latex, synthetic rubbers, polyester-polyether copolymers, polycarbonates, and other organic materials.

Additives that can be combined with a poly(ortho ester) polymer as disclosed herein to form a composition include, but are not limited to, wetting agents for improving wettability to hydrophobic surfaces, viscosity and flow control agents to adjust the viscosity and thixotropy of the mixture to a desired level, antioxidants to improve oxidative stability of the coatings, dyes or pigments to impart color or radiopacity, and air release agents or defoamers, cure catalysts, cure accelerants, plasticizers, solvents, stabilizers (cure inhibitors, pot-life extenders), and adhesion promoters.

Of particular interest for medical and pharmaceutical applications are compositions that include one or more poly(ortho ester) polymers as disclosed herein and a biologically active agent. As used herein, a "biologically active agent" is intended to be broadly interpreted as any agent capable of eliciting a response in a biological system such as, for example, living cell(s), tissue(s), organ(s), and being(s). Biologically active agents can include natural and/or synthetic agents. Thus, a biologically active agent is intended to be inclusive of any substance intended for use in the diagnosis, cure, mitigation, treatment, or prevention of disease or in the enhancement of desirable physical or mental development and conditions in a subject.

The term "subject" as used herein is taken to include humans, sheep, horses, cattle, pigs, dogs, cats, rats, mice, birds, reptiles, fish, insects, arachnids, protists (e.g., protozoa), and prokaryotic bacteria. Preferably, the subject is a human or other mammal.

A preferred class of biologically active agents includes drugs. As used herein, the term "drug" means any therapeutic agent. Suitable drugs include inorganic and organic drugs, without limitation, and include drugs that act on the peripheral nerves, adrenergic receptors, cholinergic receptors, nervous system, skeletal muscles, cardiovascular system, smooth muscles, blood circulatory system, synaptic sites, neuro-effector junctional sites, endocrine system, hormone systems, immunological system, reproductive system, skeletal system, autocoid systems, alimentary and excretory systems (including urological systems), histamine systems, transformed tissues of any of the above systems in cancer, and the like. Such conditions, as well as others, can be advantageously treated using compositions as disclosed herein.

Suitable drugs include those provided above for "Z", the therapeutic agent incorporated into the poly(ortho ester) polymers described herein.

Suitable drugs also include biologics, for example, polypeptides (which is used herein to encompass a polymer of L- or D-amino acids of any length including peptides, oligopeptides, proteins, enzymes, hormones, etc.), polynucleotides (which is used herein to encompass a polymer of nucleic acids of any length including oligonucleotides, single- and double-stranded DNA, single- and double-stranded RNA, DNA/RNA chimeras, etc.), saccharides (e.g., mono-, di-, poly-saccharides, and mucopolysaccharides), vitamins, viral agents, and other living material, radionuclides, chemotherapeutic agents, and the like. Examples include antithrombogenic and anticoagulant agents such as heparin, coumadin, protamine, and hirudin; antimicrobial agents such as antibiotics; antineoplastic agents and antiproliferative agents such as etoposide, podophylotoxin; antiplatelet agents including aspirin and dipyridamole; antimitotics (cytotoxic agents) and antimetabolites such as methotrexate, colchicine, azathioprine, vincristine, vinblastine, fluorouracil, adriamycin, and mutamycinnucleic acids; antidiabetic such as rosiglitazone maleate; and anti-inflammatory agents. Anti-inflammatory agents include glucocorticoids, their salts, and derivatives thereof, such as cortisol, cortisone, fludrocortisone, Prednisone, Prednisolone, 6α-methylprednisolone, triamcinolone, betamethasone, dexamethasone, beclomethasone, aclometasone, amcinonide, clebethasol and clocortolone.

Classes of drugs include, for example, Plasmid DNA, genes, antisense oligonucleotides and other antisense agents, peptides, proteins, protein analogs, antibodies, fusion proteins, siRNA, shRNA, miRNA, ribozymes, DNAzymes and other DNA based agents, viral and non-viral vectors, lyposomes, cells, stem cells, antineoplastic agents, antiproliferative agents, antithrombogenic agents, anticoagulant agents, antiplatelet agents, antibiotics, anti-inflammatory agents, antimitotic agents, immunosuppressants, growth factors, cytokines, hormones, and combinations thereof.

Suitable drugs can have a variety of uses including, but are not limited to, anticonvulsants, analgesics, antiparkinsons, antiinflammatories (e.g., ibuprofen, fenbufen, cortisone, and the like), calcium antagonists, anesthetics (e.g., benoxinate, benzocaine, procaine, and the like), antibiotics (e.g., ciprofloxacin, norfloxacin, clofoctol, and the like), antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, cell survival factors, chemotherapeutics, collagenase inhibitors, depressants, diagnostics, diuretics, electrolytes, enzymes, enzyme inhibitors, growth factors, hypnotics, hormones, hypoglycemics, hyperglycemics, muscle contractants, muscle relaxants, neoplastics, glycoproteins, growth factors, nucleoproteins, lipoproteins, lubricants, lubricins, mucins, ophthalmics, protease inhibitors, psychic energizers, sedatives, small molecule inhibitors, steroids sympathomimetics, parasympathomimetics, tranquilizers, urinary tract drugs, vaccines, vaginal drugs, vitamins, collagen, hyaluronic acid and derivatives, nonsteroidal anti-inflammatory drugs, angiotensin converting enzymes, polynucleotides, polypeptides, polysaccharides, and the like.

Certain embodiments include a drug selected from growth factors, receptors, and cytokines including but not limited to IGF-1, VEGF, PDGF, GDNF, GDNF analogs, BDNF, BMPs, GDF-5, EGF, FGF, HIF-1, HGF, MCP 1,2,3,or 4, SDF-1, MIP, GM-CSF, G-CSF, IL-10, CDNF, TIMPS, MIF, RANK, OPG, leptin, LIF, TIMP-1, TIMP-2, ANG-2, TGF-alpha, TGF-beta, HGH, TNF receptor, AKT, CNTF, NGF, NT3, and the like.

Other embodiments include a drug selected from hormones or related molecules including but not limited to insulin, corticotrophin, adrenocorticotrophin, growth hormone, dopamine, osteoponntin, vasoinhibitory peptide (VIP), vasopressin, epinephrine, oxytocin, estrogen or derivatives, SERMs, progesterone, estrone, cortisone, or bisphosphonates.

Certain embodiments include a drug selected from indomethacin, sulindac, diclofenal, etodolac, meclofenate, mefenamic acid, nambunetone, piroxicam, phenylgutazone, meloxicam, dexamethoasone, betamethasone, dipropionate, diflorsasone diacetate, clobetasol propionate, galobetasol propionate, amcinomide, ascomycin, baclofen, bupivacaine, beclomethasone dipropionate, betamethasone, celocoxib, curcumin, curcumin derivatives, penicillamine, fluocinomide, hydroxychloroquine, sulfasalazine, azathioprine, minocycline, cyclophosphamide, cyclosporine, leflunomide, methotrexate, etanercept, infliximab, beta-estradiol, rosiglitazone, troglitazone, pioglitazone, S-nitrosoglutathione, gliotoxin G, panepoxydone, cycloepoxydon tepoxalin, a proteasome inhibitor (e.g., bortezomib, dipeptide boronic acid, lactacystin, bisphosphonate, zolendronate, epoxomicin), antisense c-myc, triamcinolone acetonide, valdecoxib, valerate, or combinations thereof.

Certain other embodiments include a drug selected from podophyllotoxin, mycophenolic acid, teniposide, etoposide, trans-retinoic acids, 9-cis retinoic acid, 13-cis retinoic acid, rapamycin, a rapalog (e.g., Everolimus, ABT-578), camptothecin, irinotecan, topotecan, pimicrolimus, ascomycin, tacromilus, midazolam, mithramycin, mitobronitol, thiotepa, treosulfan, estramusting, chlormethine, carmustine, lomustine, busultan, mephalan, chlorambucil, ifosfamide, cyclophosphamide, doxorubicin, epirubicin, aclarubicin, daunorubicin, mitosanthrone, bleomycin, cepecitabine, cytarabine, fludarabine, cladribine, gemtabine, 5-fluorouracil, mercaptopurine, tioguanine, vinblastine, vincristine, vindesine, vinorelbine, amsacrine, bexarotene, crisantaspase, decarbasine, hydrosycarbamide, pentostatin, carboplatin, cisplatin, oxiplatin, procarbazine, paclitaxel, docetaxel, epothilone A, epothilone B, epothilone D, baxiliximab, daclizumab, interferon alpha, interferon beta, maytansine, MDT-2007, ropinerole, tranexamic acid, carbamazeprine, or combinations thereof.

Certain embodiments include a drug selected from salicylic acid, fenbufen, cortisone, ibuprofen, diflunisal, sulindac, difluprednate, prednisone, medrysone, acematacin, indomethacin, meloxicam, camptothecin, benoxinate, benzocaine, procaine, ciprofloxacin, norfloxacin, clofoctol, dexamethasone, fluocinolone, ketorolac, pentoxifylline, rapamycin, ABT-578, gabapentin, baclofen, sulfasalazine, bupivacaine, sulindac, clonidine, etanercept, pegsunercept, or combinations thereof.

It should be understood that one or more biologically active agent or drug can be admixed with the poly(ortho ester) polymers of the invention. The one or more biologically active agent or drug can be coated onto the poly(ortho ester), embedded into the polymer, simply admixed with a mixture of poly(ortho ester) polymer, etc. such that the one or more biologically active agent or drug is not covalently bound to the polymer backbone.

Compositions including a biologically active agent and a poly(ortho ester) polymer as disclosed herein and can be prepared by suitable methods known in the art. For example, such compositions can be prepared by solution processing, milling, extruding, polymerizing components including at least one hydroxy-containing compound and compounds of Formula II, Formula IV, and/or Formula IV in the presence of a biologically active agent, and combinations thereof.

Typically, the amount of biologically active agent contained by the poly(ortho ester) polymer is determined by the amount to be delivered and the time period over which it is to be delivered. Other factors can also contribute to the level of biologically active agent present, including, for example, the ability of the composition to form a uniform film on a substrate.

Compositions including poly(ortho ester) polymers as disclosed herein (e.g., with or without a biologically active agent) can further include additional components. Examples of such additional components include fillers, dyes, pigments, inhibitors, accelerators, viscosity modifiers, wetting agents, buffering agents, stabilizers, biologically active agents, polymeric materials, excipients, and combinations thereof. Alternatively, the poly(ortho ester) polymer itself can be an excipient in a composition (e.g., a pharmaceutical composition including a biologically active agent).

The compositions of the invention can include a "therapeutically effective amount" or a "prophylactically effective amount" of a polymer of the invention. A "therapeutically effective amount" refers to an amount effective, at dosages and for periods of time necessary, to achieve the desired therapeutic result, e.g., a diminishment or prevention of inflammation symptomology or disease process. A therapeutically effective amount of the polymer of the invention can vary according to factors such as the disease state, age, sex, and weight of the individual, and the ability of the polymer to elicit a desired response in the individual, reduction or elimination of pain or inflammation. A therapeutically effective amount is also one in which any toxic or detrimental effects of the polymer are outweighed by the therapeutically beneficial effects. A "prophylactically effective amount" refers to an amount effective, at dosages and for periods of time necessary, to achieve the desired prophylactic result on the disease or condition. Typically, since a prophylactic dose is used in subjects prior to or at an earlier stage of disease, the prophylactically effective amount will be less than the therapeutically effective amount.

The term "inflammation" is recognized in the art and is intended to encompass the complex series of biological responses of vascular tissues to harmful stimuli, such as pathogens, damaged cells, or irritants. Inflammation is a cascade of physiological events by the organism to remove the injurious stimuli as well as initiate the healing process for the tissue. The term "inflammation" as used herein is also intended to include neural inflammation which can be related to neuronal cell death.

Medical devices that include one or more poly(ortho ester) polymers as disclosed herein and a biologically active agent can have a wide variety of uses. In such devices, the biologically active agent is preferably disposed in the one or more polymers. As used herein, the term "disposed" is intended to be broadly interpreted as inclusive of dispersed, dissolved, suspended, or otherwise contained at least partially therein or thereon.

For example, such devices can be used to deliver a biologically active agent to a tissue by positioning at least a portion of the device including the one or more polymers proximate the tissue and allowing the one or more polymers to biodegrade and deliver the biologically active agent disposed therein. For another example, such devices can be used to control the release rate of a biologically active agent from a medical device by disposing the biologically active agent in at least one of the one or more polymers.

The present disclosure is further illustrated by the following examples. It is to be understood that the particular examples, materials, amounts, and procedures are to be interpreted broadly in accordance with the scope and spirit of the disclosure as set forth herein.

The following paragraphs enumerated consecutively from 1 through 45 provide for various aspects of the present invention. In one embodiment, in a first paragraph (1), the present invention provides a polymer comprising:

a polymer including two or more repeat units selected from a repeat unit of the formula (Formula VI):

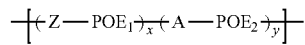

wherein each $POE_1$ and $POE_2$, independently, is represented by the formula:

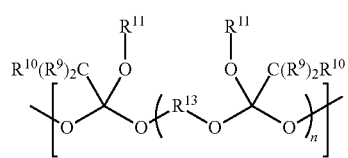

or the formula:

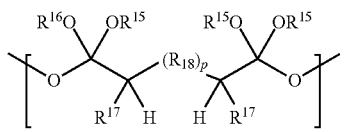

wherein:
each $R^9$, $R^{10}$, and $R^{17}$ independently represents hydrogen or an organic group;
each $R^{11}$, $R^{13}$, $R^{15}$, and $R^{16}$ independently represents an organic group;
$R^{18}$ represents oxygen or an organic group and p=0 or 1;
n=0 or 1;
each $R^{11}$ can optionally be joined with $R^{13}$ to form one or more rings;
geminal $R^{15}$ and $R^{16}$ groups can optionally be joined to each other to form rings;
each A, optionally, is —C($R^1$)($R^2$)—(C($R^5$)$_2$)$_r$—C($R^3$)($R^4$)—, —Ar$^{het}$—, —Ar$^1$C($R^6$)($R^7$)—, a group of the formula (Formula III) —Ar$^2$—C($R^8$)$_2$—Ar$^2$—(B)$_m$—, —C(=O)—, —(C=O)—R—(C=O)—, or combinations thereof;
R is an organic group;
each $R^1$, $R^2$, $R^3$, $R^4$, and $R^5$ independently represents hydrogen or an organic group, r is 0 to 20, and one or more of $R^1$, $R^2$, $R^3$, $R^4$, and $R^5$ can optionally be joined with one another to form one or more rings;
Ar$^{het}$ represents a 1,2-heteroarylene group;
Ar$^1$ represents a 1,2- or a 1,3-arylene group, or a 1,2- or a 1,3-heteroarylene group, $R^6$ and $R^7$ independently represent hydrogen or an organic group, and $R^6$ and/or $R^7$ can optionally be joined with each other or with the Ar$^1$ group to form one or more rings;
each Ar$^2$ independently represents an arylene group, each $R^8$ independently represents an organic group, B represents an aromatic-containing organic group having a linking oxygen attached to the aromatic ring, and m=0 or 1;
each x is 1 to about 200;
each y, if present, is 0 to about 200;
x+y is from 2 to about 400; and
each Z is a therapeutic agent containing at least one phenoxy residue and at least one hydroxyl residue or at least a second phenoxy residue.

2. The polymer of paragraph 1, wherein Z is the residue of Apigenin, Astringin, (+)-1-Acetoxypinoresinol, Arzanol, Biochanin A, Campesterol, Catechin, Catechin gallate, Chrysin, Coumestrol, Curcumin, Cyanidin, Daidzein, Daphnetin, Delphinidin, Desoxyrhapontigenin, 7,2'-Dihydroxy-4'-methoxyisoflavanol, Ellagic acid, Epicatechin, Epigallocatechin, Epigallocatechin gallate, Eriodictyol, Fisetin, Gallocatechin, Gallocatechin gallate, Genistein, Gingerol, Glycitein, Helipyrone, Hesperidin, Hespertin, 2'-Hydroxyformoronetin, 2-Hydroxyisoflavanone, Hydroxytyrosol, Isoliquiritigenin, Isorhamnetin, Isorhapontin, Kaempferol, Lariciresinol, Leucopelargonidin, Liquiritigenin, Luteolin, Malvidin, Maringenin, Matairesinol, Methylarzanol, Myricetin, Naringenin, Oleuropein, Oxyresveratrol, Pelargonidin, Peonidin, Petunidin, Piceatannol, Piceid, Pinoresiniol, Pinostilbene, Pinostilbenoside, Proanthocyanidin, Pterostilbene, Punicalagins, Quercetin, Resveratrol, Resveratroloside, Rhaponticin, Rhapontigenin, Rutin, Secoiroidoid, Secoisolariciresinol, Silibinin, Silybin, Semimyrtucommulone, Tangeritin, 4,2',4',6'-Tetrahydroxy-chalcone, Theaflavins, Thearubigin, 4,4',6'-Trihydroxyaurone, Tyrosol, Vanillyl alcohol, (−)-Vestitone, Xanthohumol or combinations thereof.

3. The polymer of paragraph 1 wherein the repeat unit of the formula (Formula VI) is represented by Formula VIa:

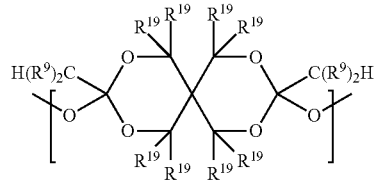

wherein:
each $R^9$ and $R^{19}$ independently represents hydrogen or an organic group.

4. The polymer of paragraph 3 wherein each $R^{19}$ represents hydrogen and each $R^9$ independently represents hydrogen or methyl.

5. The polymer of any of paragraphs 1 through 4, wherein Z is a Resveratrol or Curcumin residue.

6. The polymer of any of paragraphs 1 through 5, wherein A is 1,4-cyclohexanedimethanol or 1,6-hexanediol.

7. The polymer of any of paragraphs 1 through 6, wherein the molecular weight is at least 10,000.

8. The polymer of any of paragraphs 1 through 7, wherein the polymer is stable at 37 °C. in an aqueous solution for at least 7 days.

9. The polymer of any of paragraphs 1 through 8, wherein the polymer is biodegradable.

10. A method of preparing a polymer, the method comprising:
combining components comprising:
at least one hydroxy-containing compound of the formula (Formula I)

HO—Z—OH, or a mixture of Formula I and

HO—A—OH, and (Formula Ia)

at least one orthoester of the formula (Formula II)

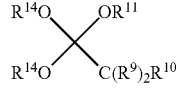

under conditions effective to polymerize at least a portion of the orthoester; and
removing byproducts comprising $R^{14}$OH;
wherein each $R^9$ and $R^{10}$ independently represents hydrogen or an organic group;
each $R^{11}$ and $R^{14}$ independently represents an organic group;
each A, optionally, is —C($R^1$)($R^2$)—(C($R^5$)$_2$)$_r$—C($R^3$)($R^4$)—, —Ar$^{het}$—, —Ar$^1$C($R^6$)($R^7$)—, a group of the formula (Formula III) —Ar$^2$—C($R^8$)$_2$—Ar$^2$—(B)$_m$—, —C(=O)—, —(C=O)—R—(C=O)—, or combinations thereof;
R is an organic group;
each $R^1$, $R^2$, $R^3$, $R^4$, and $R^5$ independently represents hydrogen or an organic group, r is 0 to 20, and one or more of $R^1$, $R^2$, $R^3$, $R^4$, and $R^5$ can optionally be joined with one another to form one or more rings;

Ar$^{het}$ represents a 1,2-heteroarylene group;

Ar$^1$ represents a 1,2- or a 1,3-arylene group, or a 1,2- or a 1,3-heteroarylene group, R$^6$ and R$^7$ independently represent hydrogen or an organic group, and R$^6$ and/or R$^7$ can optionally be joined with each other or with the Ar$^1$ group to form one or more rings;

each Ar$^2$ independently represents an arylene group, each R$^8$ independently represents an organic group, B represents an aromatic-containing organic group having a linking oxygen attached to the aromatic ring, and m=0 or 1; and each Z is a therapeutic agent containing at least one phenoxy residue and at least one hydroxyl residue or at least a second phenoxy residue.

11. The method of paragraph 10, wherein Z is a Resveratrol or Curcumin residue.

12. The method of either paragraph 10 or 11, wherein A is 1,4-cyclohexanedimethanol or 1,6-hexandiol.

13. The method of any of paragraphs 10 through 12, wherein the molecular weight of the polymer is at least 10,000.

14. The method of any of paragraphs 10 through 13, wherein removing byproducts comprises removing byproducts under azeotropic conditions.

15. The method of any of paragraphs 10 through 14, wherein combining components further comprises combining a polymerization agent.

16. The method of paragraph 15, wherein the polymerization agent comprises a Lewis acid or a Brønsted-Lowry acid.

17. The method of paragraph 16, wherein the Brønsted-Lowry acid is hydrochloric acid, p-toluenesulfonic acid, methanesulfonic acid, trifluoromethanesulfonic acid, camphorsulfonic acid, or combinations thereof.

18. The method of paragraph 16, wherein the Lewis acid comprises Al, Fe, B, Zn, Sb, Ti, Cu, Sn, Si, or combinations thereof.

19. The method of any of paragraphs 10 through 18, wherein combining components further comprises combining an additional polymerizable compound selected from ketene acetals, monofunctional orthoesters, polyfunctional orthoesters, imagable compounds, compounds having latent reactive sites, or combinations thereof.

20. A method of forming a biodegradable medical device, the method comprising preparing a polymer according to the method of any of paragraphs 10 through 19, wherein the components are combined in a mold.

21. A polymer prepared by a method of any of paragraphs 10 through 19.

22. A method of preparing a polymer comprising combining components comprising at least one hydroxy-containing compound of the formula (Formula I) HO—Z—OH or a mixture of Formula I and a compound of the formula (Formula Ia) HO—A—OH and at least one ketene acetal under conditions effective to polymerize at least a portion of the at least one ketene acetal, wherein the at least one ketene acetal is:

a compound of the formula (Formula IV)

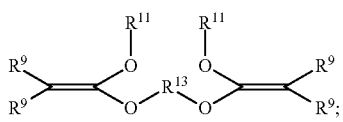

or a compound of the formula (Formula V)

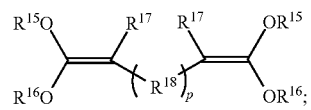

or combinations thereof;

wherein:

each R$^9$ and R$^{17}$ independently represents hydrogen or an organic group;

each R$^{11}$, R$^{13}$, R$^{15}$, and R$^{16}$ independently represents an organic group;

R$^{18}$ represents oxygen or an organic group and p=0 or 1;

each R$^{11}$ can optionally be joined with R$^{13}$ to form one or more rings;

geminal R$^{15}$ and R$^{16}$ groups can optionally be joined to each other to form rings;

each A, optionally, is —C(R$^1$)(R$^2$)—(C(R$^5$)$_2$)$_r$—C(R$^3$)(R$^4$)—, —Ar$^{het}$—, —Ar$^1$C(R$^6$)(R$^7$)—, a group of the formula (Formula III) —Ar$^2$—C(R$^8$)$_2$—Ar$^2$—(B)$_m$—, —C(═O)—, —(C═O)—R—(C═O)—, or combinations thereof;

R is an organic group;

each R$^1$, R$^2$, R$^3$, R$^4$, and R$^5$ independently represents hydrogen or an organic group, r is 0 to 20, and one or more of R$^1$, R$^2$, R$^3$, R$^4$, and R$^5$ can optionally be joined with one another to form one or more rings;

Ar$^{het}$ represents a 1,2-heteroarylene group;

Ar$^1$ represents a 1,2- or a 1,3-arylene group, or a 1,2- or a 1,3-heteroarylene group, R$^6$ and R$^7$ independently represent hydrogen or an organic group, and R$^6$ and/or R$^7$ can optionally be joined with each other or with the Ar$^1$ group to form one or more rings;

each Ar$^2$ independently represents an arylene group, each R$^8$ independently represents an organic group, B represents an aromatic-containing organic group having a linking oxygen attached to the aromatic ring, and m=0 or 1; and each Z is a therapeutic agent containing at least one phenoxy residue and at least one hydroxyl residue or at least a second phenoxy residue.

23. The method of paragraph 22, wherein the compound of the formula (Formula IV) is represented by Formula IV(a):

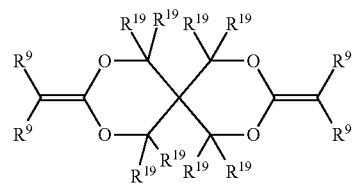

wherein each R$^9$ and R$^{19}$, independently represents hydrogen or an organic group.

24. The method of paragraph 23 wherein each R$^9$ and R$^{19}$ represents hydrogen.

25. The method of paragraph 22, wherein Z is a Resveratrol or Curcumin residue.

26. The method of any of paragraphs 22 through 25, wherein A is 1,4-cyclohexanedimethanol or 1,6-hexandiol.

27. The method of any of paragraphs 22 through 26, wherein the molecular weight of the polymer is at least 10,000.

28. The method of any of paragraphs 22 through 27, wherein removing byproducts comprises removing byproducts under azeotropic conditions.

29. The method of any of paragraphs 22 through 28, wherein combining components further comprises combining a polymerization agent.

30. The method of paragraph 29, wherein the polymerization agent comprises a Lewis acid or a Brønsted-Lowry acid.

31. The method of paragraph 30, wherein the Brønsted-Lowry acid is hydrochloric acid, p-toluenesulfonic acid, methanesulfonic acid, trifluoromethanesulfonic acid, camphorsulfonic acid, or combinations thereof.

32. The method of paragraph 30, wherein the Lewis acid comprises Al, Fe, B, Zn, Sb, Ti, Cu, Sn, Si, or combinations thereof.

33. The method of any of paragraphs 22 through 32, wherein combining components further comprises combining an additional polymerizable compound selected from ketene acetals, monofunctional orthoesters, polyfunctional orthoesters, imagable compounds, compounds having latent reactive sites, or combinations thereof.

34. A polymer prepared by a method of any of paragraphs 22 through 33.

35. A method of forming a biodegradable medical device, the method comprising preparing a polymer according to any of paragraphs 22 through 33, wherein the components are combined in a mold.

36. A method of preparing a biodegradable medical device, the method comprising:
providing a medical device; and
applying one or more polymers according any of paragraphs 22 through 33 to at least a portion of the device.

37. A method to prevent, decrease or alleviate pain or inflammation comprising the step of administering to a subject in need thereof, a therapeutically effective amount of a polymer of any of paragraph 1 through 34, such that the pain or inflammation is prevented, decreased, or alleviated.

38. A method to treat benign growth or cancer related neoplasms comprising the step of administering to a subject in need thereof, a therapeutically effective amount of polymer of any of paragraph 1 through 34 such that the condition is treated.

39. A method to prevent, decrease or alleviate pain or inflammation comprising the step of administering to a subject in need thereof, a therapeutically effective amount of a polymer of any of paragraph 1 through 34 wherein the polymeric composition is delivering an encapsulated or commixed therapeutic, such that the pain or inflammation is prevented, decreased, or alleviated.

40. A method to treat benign growth or cancer-related neoplasm comprising the step of administering to a subject in need thereof, a therapeutically effective amount of polymer of any of paragraph 1 through 34 wherein the polymeric composition is delivering an encapsulated or commixed therapeutic, such that the benign or oncological condition is treated.

41. The polymer of any of paragraphs 1 through 9, wherein the polymer further contains a drug selected from baclofen, bupivacaine or midazolam to form a composition.

42. The composition of paragraph 41, wherein the drug is admixed with the polymer.

43. The method of any of paragraphs 37 through 40, further comprising administering the composition of paragraph 41 or 42.

44. The method of paragraph 39, wherein the inflammation is neural inflammation.

45. The method of paragraph 44, wherein the neural inflammation is associated with neuronal cell death.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1

Synthesis in general: All reactions were carried out under nitrogen in a dry box. Glassware and stir bars were dried in a 115° C. oven overnight. In a round bottom flask, the phenolic material was dissolved in tetrahydrofuran (THF), and to this, 9,-diethylidene-2,4,8,10-tetraoxaspiro [5,5] undecane (DETOSU) was added. After all solid materials were in solution upon magnetically stirring, 1 mL of 1 per cent p-toluenesulfonic acid solution in THF was charged from a pipette. The 1,6-trans-hexanedimethanol (t-CHDM) and/or 1,6 hexanediol (HD) were later added and stirring continued overnight (about 16 hours) at the room temperature. The loading details for the Examples I, II, III and IV were listed in the following table. The reactions for the Example I, II and V were found to be gelled after mixing all the materials, and the resulting polymers seemed not to be soluble in THF.

|  | DETOSU (gram) | Curcumin (gram) | Resveratrol (gram) | tCHDM (gram) | HD (gram) | TH (mL) | Mw (g/mol) | Mn (g/mol) |
|---|---|---|---|---|---|---|---|---|
| Example I* | 15.0370 | 2.6372 | 0 | 4.5961 | 3.766 | 50 | ND | ND |
| Example II* | 15.0306 | 1.2363 | 0 | 4.8605 | 3.987 | 50 | ND | ND |
| Example III# | 10.0407 | 1.8037 | 0 | 6.1047 | 0 | 50 | 24860 | 6800 |
| Example IV$ | 2.960 | 0 | 0.496 | 1.530 | 0 | 3 | 12900 | 3100 |
| Example V* | 15.5348 | 2.4847 | 0 | 9.6219 | 0 | 50 | ND | ND |

Note:
*Curcumin from Spectrum, Inc. Lot Number VD1005.
Curcumin from Aldrich, Catalog number 238384.
$Resveratrol from Aldrich, catalog number R5010.
ND = not determined Stability and Elution The material from the Example IV was made into microshopheres (5 mg, mean size: 15 to 20 micron) and was added to a 0.0067 M phosphate buffered saline solution (PBS) (20 mL, pH 7.4) The microspheres were prepared in a manner similar to that reported by Hongkee Sah, J. Controlled Release 47 (1997) 233-245, Microencapsulation techniques using ethyl acetate as a dispersed solvent: effects of its extraction rate on the characteristics of PLGA microspheres. The vial was shaken in a 37° C. incubator at 100 rpm. The microspheres were in free suspension after one week. At this point, high pressure liquid chromatography (HPLC) (conditions provided below) revealed no detectable resveratrol present in the buffer solution indicating a very slow release into aqueous solutions or a high stability of the polymer in aqueous solutions.

In a separate experiment, the microsphere (8.5 mg) or the polymer (10.5 mg) was dissolved in THF (10 mL) with 1 N hydrochloride (100 microliter). Clear solutions formed instantaneously. The loadings of resveratrol in the microsphere and the polymer were 11.9% and 11.2 percent, respectively, from the HPLC analyses (as noted in table below) on the solution indicating a very slow release or potential insolubility in PBS. Note that by histopathology these same microspheres were not obvious in the rat knee by 28 days (see Example 3

| | |
|---|---|
| Mobile phase A | Acetonitrile with 0.1% acetic acid |
| Mobile phase B | Water with 0.1% acetic acid |
| Isocratic | 60% mobile phase A with 40% mobile phase B |
| Detector | UV absorbency at 265 nm |
| Auto injector | 10 micro liter |
| Total flow rate | 0.3 mL/min |
| Column | ProntoSIL, C18, 4.6 × 150 mm, 5 micron |
| Column Temperature | 30° C. |
| Sample Temperature | 25° C. |
| Run time | 35 minutes |
| Instrument | Agilent ChemStation |

Example 2

Polyphenolic Polymers are Nontoxic and Non-Inflammatory in vitro

Degraded polymer products from the above polymers were compared with PDL and PDLG breakdown products for their toxicity and ability to provoke IL-1 beta cytokine secretion from differentiated human chondrocytes and a human synovial cell line.

Background:

Polyphenolic polymers could be used to treat diseases locally, for example in osteoarthritis. There is significant evidence that certain types of polymers elicit an inflammatory response from macrophages or other cell types, thus indicating a potential problem with biocompatibility. One test for inflammatory potential is to measure activation of the NFκB pathway, a pathway intimately involved in the generation of cytokines and enzymes that play a role in the pathogenesis of osteoarthritis.

It is known that the activation of NFκB can lead to increased expression of IL-1β, a cytokine capable of potentiating an inflammatory response by binding to the IL-1 receptor and further activating NFκB. IL-1 beta is primarily produced by monocytes, macrophages, T cells and synoviocytes, but also other cell types, such as articular chondrocytes.

To insure that the therapeutic polymers were not only nontoxic, but were also not pro-inflammatory, the polymeric degradation products were screened for their ability to elicit IL-1β production both from two cell types representative of those found in the joint space.

Materials:

Normal human articular chondrocytes—Lonza, Cat#CC-2250

Human sarcoma synoviocytes—ATCC, Cat#HTB-93

T-flasks—BD/VWR, Cat#353136, 47443-882

Cell Titer Glo—Promega, Cat #G7571

Cell Titer Blue—Promega

Cell culture treated 96 well plate (V-bottom and flat)

DMEM+Glutamax (Gibco)+10% FBS (Hyclone)

Chondrocyte differentiation media—Lonza Cat#CC-3225

Chondrocyte basal media—Lonza Cat#CC-3216

1N NaOH solution

QuantiGlo Human IL-1/IL-1F2 Immunoassay (R and D Systems; # QLB00B)

Multi-channel pipetteman 0.1% A Saponin in HBSS++

TNF alpha (Biosource; #PHC3016)

POE1, POE2, PLA, and PLDA (Lakeshore Biomaterials; table 1)

Polycurcumin and Polyresveratrol breakdown products (prepared internally; Table 2) Microspheres were prepared as indicated above Polymer Forced Degradation Method:

Forced degradation was performed on various polymers in order to evaluate in vitro biocompatibility of the polymer partial degradation products. The polymers were degraded by adding 1 gram of polymer to a vial with 5-ml of deionized water. The suspension was then placed in an 85° C. oven and samples for each polymer were removed after 2 and 5 days. The latter time was the point at which either all solid was solubilized or there was no additional change to solubility. After the solutions cooled to room temperature they were sterile filtered into 50-ml polypropylene conical tubes, frozen on liquid nitrogen, and freeze-dried for 3 days. Samples were stored at −40° C. until use.

The polymers tested are listed in the following table along with sample references. Complete degradation solutions were prepared from monomers.

TABLE 1

| Polymer: | Lot: | Sample: | Reference: |
|---|---|---|---|
| PDLG8515-7E | LP225 | 2 days at 85° C. | 14027-28A-2d |
| Poly(D,L-lactide-co-glycolide)$_{85/15}$ | | 5 days at 85° C. | 14027-28A-5d |
| PDL100-7E | LP316 | 2 days at 85° C. | 14027-28B-2d |
| Poly(D,L-lactide) | | 5 days at 85° C. | 14027-28B-5d |
| POE1-tCHDM$_{54}$HD$_{45}$DET$_1$ | 13830-06 | 2 days at 85° C. | 14027-28C-2d |
| Polyorthoester with 54% transcyclohexanedimethanol, 45% 1,6 hexanediol, 1% diethyltartrate | | 5 days at 85° C. | 14027-28C-5d |
| POE2-tCHDM$_{100}$ | 12811-55 | 2 days at 85° C. | 14027-28D-2d |
| Polyorthoester with 100% transcyclohexanedimethanol | | 5 days at 85° C. | 14027-28D-5d |

Forced degradation was performed on polycurcumin and polyresveratrol in order to evaluate in vitro biocompatibility of the polymer partial degradation products. The polymers were degraded by adding 0.1 grams of polymer to a vial with 5-ml of deionized water. The suspension was then placed in an 85° C. oven and samples for each polymer were removed at various time points. After the solutions cooled to room temperature they were sterile filtered into 50-ml polypropylene conical tubes, frozen on liquid nitrogen, and freeze-dried for 3 days. Samples were stored at −40° C. until use. The polymers tested are listed in the following table along with sample references.

TABLE 2

| Polymer: | Lot: | Sample: | Reference: |
|---|---|---|---|
| Polycurcumin | 13358-72 | 2 days at 85° C. | 14027-70A |
|  |  | 5 days at 85° C. | 14027-70B |
| Polyresveratrol | 13358-54 | 1 days at 85° C. | 14027-70C |
|  |  | 2 days at 85° C. | 14027-70D |

Cell Culture Methods:

Four to five weeks before the start of the assay, primary isolates of human chondrocytes were seeded, amplified, finally dissociated and pelleted in differentiation medium in V-bottom 96 well plates. The pellets were allowed to differentiate for three to four weeks prior to the start of the assay. Synoviocytes were amplified and then seeded in 96 well plates (10,000 cells/well) the day before the assay was performed.

On the day of testing, all polymer degradation products were weighed, resuspended and diluted in complete media. To decide upon concentrations of products for testing, the amount of polymer that would be present in the joint space at any one time was estimated. The maximum concentration of polymer degradation products in the joints of rodents injected with 50 ul of 1.5 mg/ml microspheres, assuming a 10 ul joint space volume after equilibration and complete degradation in one day, would be approximately 7.5 mg/ml. As the polymers degraded over a period of days or weeks, 4 mg/ml was tested as a maximum load for PDL and PDLG byproducts. The POE polyphenolic polymers were tested also at higher concentrations so that a toxic endpoint could be established.

Cells or micropellets were treated with the degradation products for 4-6 hours, supernatants removed for IL-1B ELISA and products reapplied. Viability was then tested at 24 hours using Cell Titer Glo for synoviocytes and Cell Titer Blue for chondrocytes. It was found that the shorter application time allowed for significant stimulation of IL-1B, while 24 hours was sufficiently long to detect differences in toxicity between the polymers.

Treatment of cells or pellets with 0.1% saponin was used as a positive control for viability. A standard curve with purified IL-1 β was run with each assay (not shown). Comparisons with cells treated with normal medium alone were performed using a one-way ANOVA followed by the Holm Sidek post hoc test. *=Statistically significant ($p<0.05$) for all reported data. PDL and PDLG complete degradation products were tested twice at the higher concentrations.

Results and Discussion:

PDLG and PDL were in general more toxic and were also found to elicit more IL-1 β secretion than the other polymers tested, particularly when used to treat the synoviocytes (FIGS. 1 through 4). Less toxicity was observed with the pellets, which can be due to the fact that the chondrocytes are less metabolically active and thus not as susceptible to assault.

Figure 3:
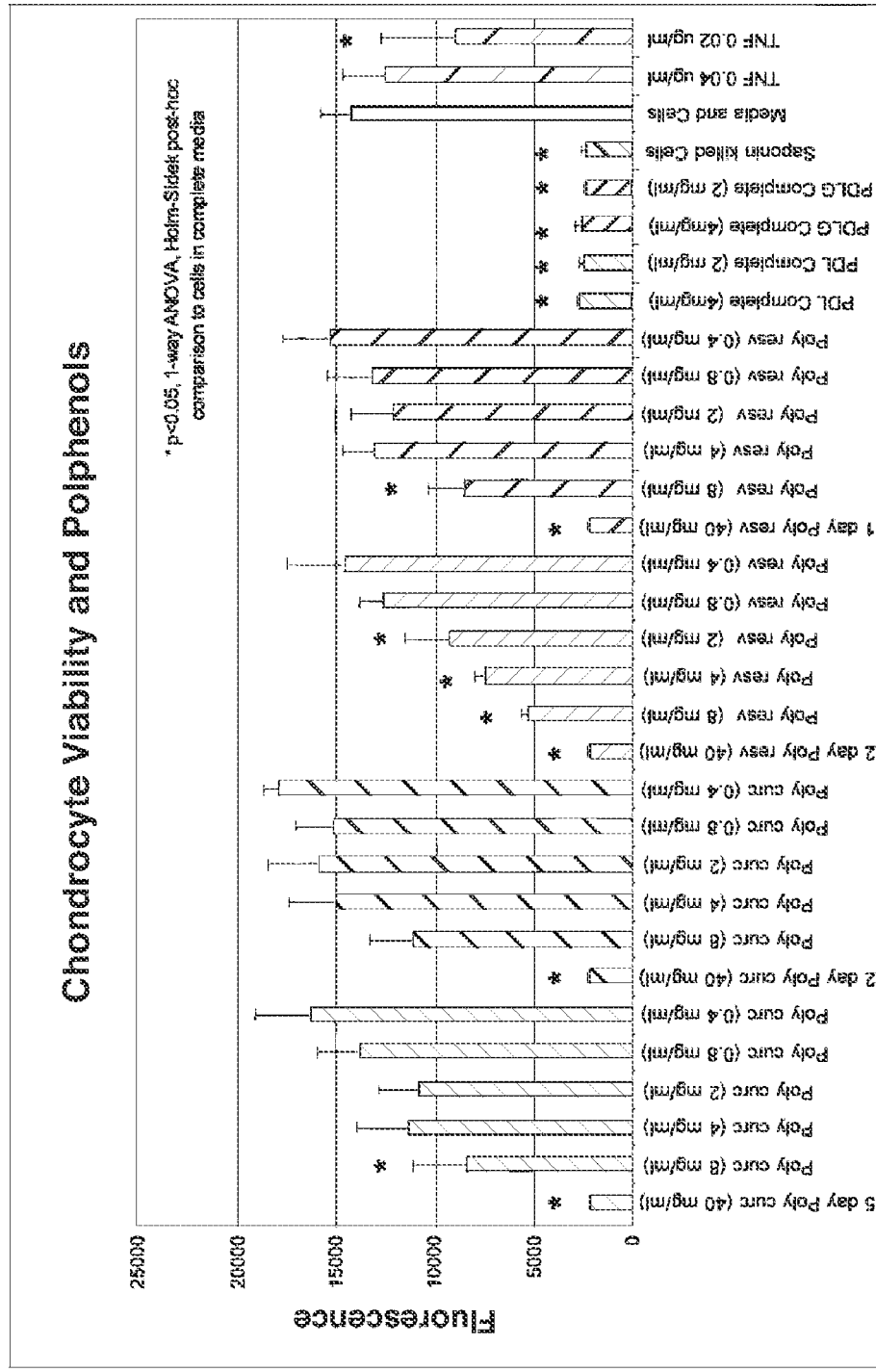
FIG. 3 depicts the effect of polymer breakdown products on differentiated chondrocyte viability measured after 24 hours of exposure. * Significantly different p<0.05 Holm-Sidek post-hoc comparison to cells in media.
Figure 4:
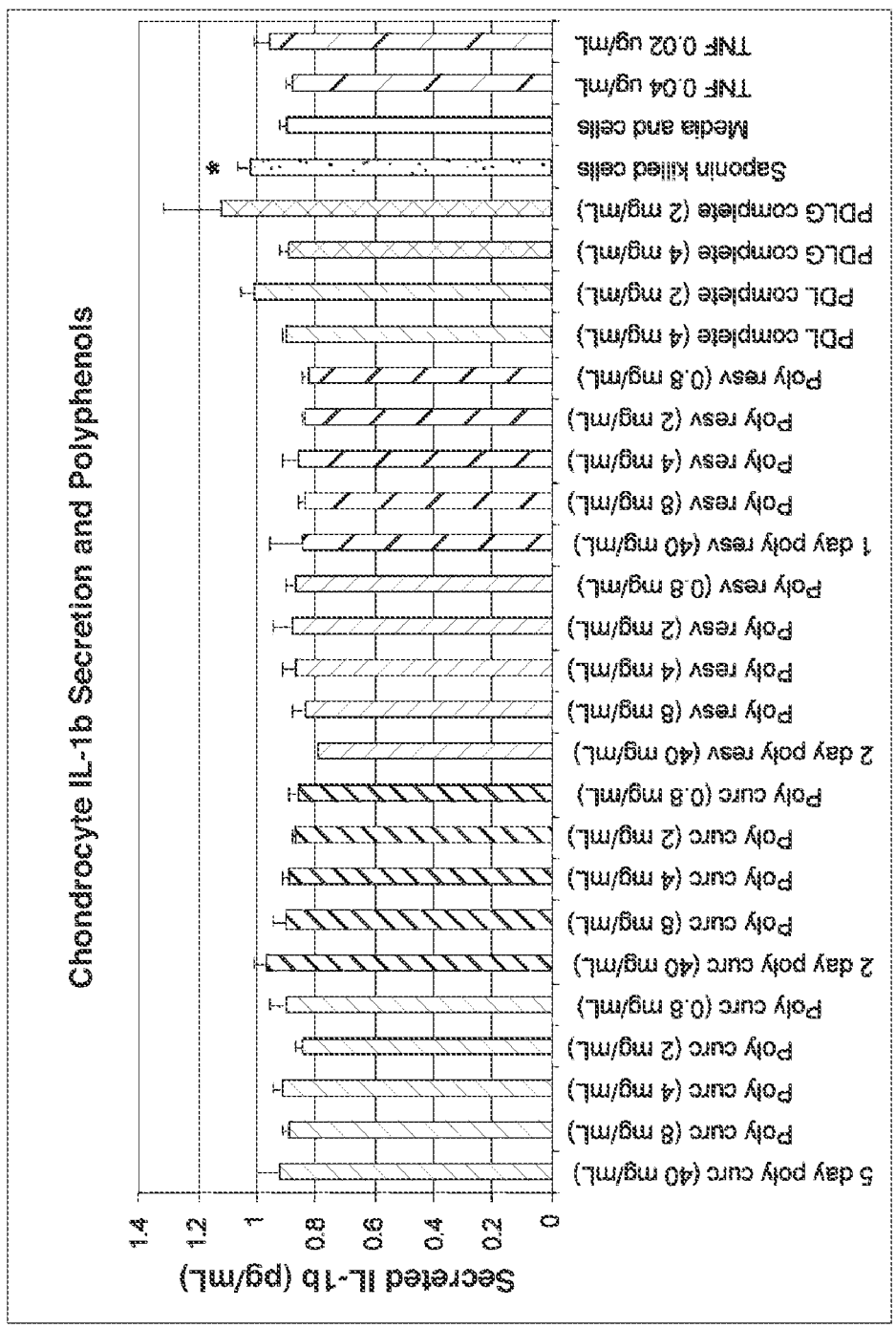
FIG. 4 demonstrates the effect of polymer breakdown products on IL-1b secretion from differentiated human chondrocytes. * Significantly different p<0.05 Holm-Sidek post-hoc comparison to cells in media.

PDLG and PDL 2, 5 day and complete breakdown products induced significant IL-1β production and toxicity at 4 mg/ml (FIGS. 1 through 4 and not shown). In some cases the stimulation of IL-1 β secretion was over 50-fold that of controls. The same level of toxicity could not be attained with the polyphenolic polymer breakdown products unless applied at 5-10 times this concentration (FIGS. 1 and 3). Since IL-1β and the associated NFKB pathway contribute significantly to the pathogenesis of disease, this finding provides that the polyphenolic polymers are superior for use in local delivery strategies.

It was noted that IL-1 β production could be stimulated by activation of the mitogen activated protein kinase (MAP kinase) pathway independently of stimulation by NFκB. MAP kinase also plays a role in the inflammatory component of osteoarthritis, although due to safety concerns MAP kinase inhibitors are not used to treat arthritis. If the PDL or PDLG polymers are stimulating inflammation through activation of this enzyme, it may be of more serious concern, as a delivered anti-inflammatory would not likely serve to mitigate this response.

Conclusion:

The results of these experiments indicate that the polyphenolic polymers tested are less inflammatory and less toxic than other commonly tested polymeric compositions.

Example 3

Polyphenolic Microspheres (as Described Above) for Local Delivery to the Joint, an in vivo Assessment of Pain and Toxicity in an Osteoarthritis Model Study Design and Methods: Animals (10/group), housed 2-3/cage, were anesthetized with Isoflurane and the right knee area prepared for surgery. A skin incision was made over the medial aspect of the knee and the medial collateral ligament exposed by blunt dissection, and then transected. The medial meniscus was cut through the full thickness to simulate a complete tear. The skin was closed with a suture. Dosing with 50 ul of a 1.5 mg/ml solution polymeric microspheres by the intra-articular route was done on day 7 after surgery in all groups except group 1 (pain control) which was dosed sc, q.d. on days 7-28 only for purposes of pain testing.

Pain response testing was accomplished using the Incapacitance meter on test days for normal values (pre-surgery), day 7 post-surgery (prior to treatment), 1 hour post-injection of sc doses (groups 1) or 3 hours post-injection (IA groups, groups 2-8) and then again at 24 hrs post treatment (the next day) then again on days 11, 14, 21 and 28 at 1 hr post treatment (group 1).

Animals were placed in the plexiglass housing of the incapacitance meter and allowed to acclimate for approximately 5 minutes or until the rat appeared to be calmly standing with both feet on the force plates. The position of the animal was such that each hind paw rests on a separate force plate. The force exerted by each hind paw was averaged over a 1 second interval, and the mean of three readings constituted 1 data point. The change in hind paw weight distribution was determined by the ratio of weight bearing for right and left limbs and as a % weight bearing for the right hind limb (1, 2) 1. Bove S. E., et al. Weight bearing as a measure of disease progression and efficacy of anti- inflammatory compounds in a model of monosodium iodoacetate-induced osteoarthritis. Osteoarthritis Cartilage. 2003; 11: 821-830. 2. Bove S. E., et al. Surgically induced osteoarthritis in the rat results in the development of both osteoarthritis-like joint pain and secondary hyperalgesia. Osteoarthritis Cartilage. 2006; 10: 1041-1048.

On day 28 rats were euthanized, synovial lavages performed on right knee using 100 µl of saline (centrifuge and collect supernatant) and then the right (operated) knee joint trimmed of muscle and connective tissue and collected into 10% neutral buffered formalin. The patella was removed to allow proper fixation of the joints. The left (normal) knee from rats 1-5 of group 1 was also lavaged and collected into formalin for normal staining controls.

Following 3 days in 10% formic acid decalcifier, the operated joints were cut into two approximately equal halves in the frontal plane and embedded in paraffin. Three sections were cut from each operated knee at approximately 200 !m steps and stained with toluidine blue. A single section was cut from each of the 5 left knees from the control group and stained with toluidine blue. All 3 sections of each knee were analyzed microscopically and a total joint score obtained. The total joint score took into account the histopathological disposition of the cartilage, bone, ligament and synovium and was assessed by conventional histopathological criteria.

Figure 5:
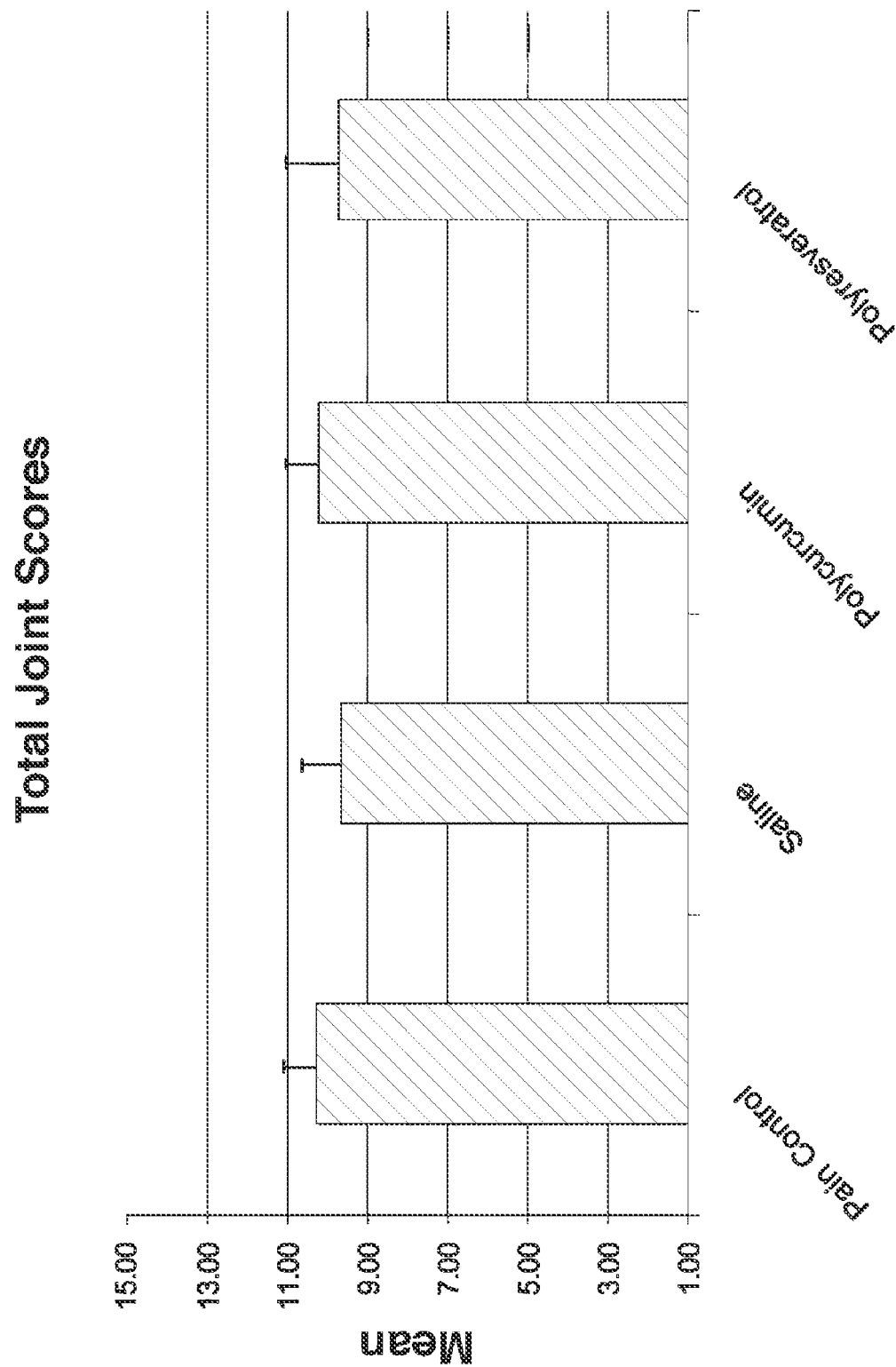
FIG. 5 provides total joint scores in the medial meniscal tear model of osteoarthritis of the rat following injection of polymeric microspheres (day 28). Animals were treated with the polycurcumin microspheres or animals were treated with the polyresveratrol microspheres described in the Examples. No histopathological changes or signs of toxicity were noted with either polyphenolic microspheres alone as compared to the saline controls. The pain control was treated with an analgesic alone.

Results:

Animals treated with either polycurcumin or polyresveratrol microspheres bore significantly more weight on their affected legs as compared to controls and measured by incapacitance testing 14 days after treatment. In addition, the polyphenolic compounds did not negatively affect the histology of the osteoarthritic joint as measured by total joint score after 28 days (FIG. 5).

Conclusions:

These polyphenolic microspheres can be used to treat joint pain and were not toxic at the concentrations tested in this osteoarthritis model.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A polymer comprising:
a polymer including two or more repeat units selected from a repeat unit of the formula (Formula VI):

$$-[-Z-POE_1)_{x}-(A-POE_2)_{y}-]-$$

wherein each $POE_T$ and $POE_2$, independently, is represented by the formula:

$$R^{10}(R^9)_2C \diagdown O \diagdown \overset{R^{11}}{\underset{}{\diagdown}} O \diagdown \overset{R^{11}}{\underset{}{\diagdown}} O \diagdown C(R^9)_2R^{10}$$

or the formula:

$$\{O \diagdown \overset{R^{16}O \quad OR^{15}}{\underset{R^{17} \quad H}{\diagdown}} (R_{18})_p \overset{R^{15}O \quad OR^{15}}{\underset{H \quad R^{17}}{\diagdown}} O\}$$

wherein:
each $R^9$, $R^{10}$, and $R^{17}$ independently represents hydrogen or an organic group;
each $R^{11}$, $R^{13}$, $R^{15}$, and $R^{16}$ independently represents an organic group;
$R^{18}$ represents oxygen or an organic group and p =0 or 1;
n =0 or 1;
each $R^{11}$ can optionally be joined with $R^{13}$ to form one or more rings;
geminal $R^{15}$ and $R^{16}$ groups can optionally be joined to each other to form rings;
each A, optionally, is $—C(R^1)(R^2)—(C(R^5)_2)^r$,$—C(R^3)(R^4)—$,$—Ar^{het}—$, $—Ar^1C(R^6)(R^7)—$, a group of the formula (Formula III) $—Ar^2—C(R^8)_2—Ar^2—(B)_m—$, $—C(=O)—$, $—(C=O)—R—(C=O)—$, or combinations thereof;
R is an organic group;
each $R^1$, $R^2$, $R^3$, $R^4$, and $R^5$ independently represents hydrogen or an organic group, r is 0 to 20, and one or more of $R^1$, $R^2$, $R^3$, $R^4$, and $R^5$ can optionally be joined with one another to form one or more rings;
$Ar^{het}$ represents a 1,2-heteroarylene group;
$Ar^1$ represents a 1,2- or a 1,3-arylene group, or a 1,2- or a 1,3-heteroarylene group, $R^6$ and $R^7$ independently represent hydrogen or an organic group, and $R^6$ and/or $R^7$ can optionally be joined with each other or with the $Ar^1$ group to form one or more rings;
each $Ar^2$ independently represents an arylene group, each $R^8$ independently represents an organic group, B represents an aromatic-containing organic group having a linking oxygen attached to the aromatic ring, and m =0 or 1;
each x is 1 to about 200;
each y, if present, is 0 to about 200;
x +y is from 2 to about 400; and
each Z is a therapeutic agent containing at least one phenoxy residue and at least one hydroxyl residue or at least a second phenoxy residue.

2. The polymer of claim 1, wherein Z is the residue of Apigenin, Astringin, (+)-1-Acetoxypinoresinol, Arzanol, Biochanin A, Campesterol, Catechin, Catechin gallate, Chrysin, Coumestrol, Curcumin, Cyanidin, Daidzein, Daphnetin, Delphinidin, Desoxyrhapontigenin, 7,2'-Dihydroxy-4'-methoxyisoflavanol, Ellagic acid, Epicatechin, Epigallocatechin, Epigallocatechin gallate, Eriodictyol, Fisetin, Gallocatechin, Gallocatechin gallate, Genistein, Gingerol, Glycitein, Helipyrone, Hesperidin, Hespertin, 2'-Hydroxyformoronetin, 2-Hydroxyisoflavanone, Hydroxytyrosol, Isoliquiritigenin, Isorhamnetin, Isorhapontin, Kaempferol, Lariciresinol, Leucopelargonidin, Liquiritigenin, Luteolin, Malvidin, Maringenin, Matairesinol, Methylarzanol, Myricetin, Naringenin, Oleuropein, Oxyresveratrol, Pelargonidin, Peonidin, Petunidin, Piceatannol, Piceid, Pinoresiniol, Pinostilbene, Pinostilbenoside, Proanthocyanidin, Pterostilbene, Punicalagins, Quercetin, Resveratrol, Resveratroloside, Rhaponticin, Rhapontigenin, Rutin, Secoirodoid, Secoisolariciresinol, Silibinin, Silybin, Semimyrtucommulone, Tangeritin, 4,2',4',6'-Tetrahydroxy-chalcone, Theaflavins, Thearubigin, 4,4',6'-Trihydroxyaurone, Tyrosol, Vanillyl alcohol, (−)-Vestitone, Xanthohumol or combinations thereof 3. The polymer of claim 1 wherein the repeat unit of the formula (Formula VI) is represented by Formula VIa:

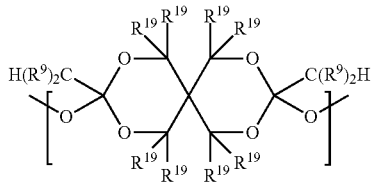

wherein:
each $R^9$ and $R^{19}$ independently represents hydrogen or an organic group.

4. The polymer of claim 3 wherein each $R^{19}$ represents hydrogen and each $R^9$ independently represents hydrogen or methyl.

5. The polymer of claim 1, wherein Z is a Resveratrol or Curcumin residue.

6. The polymer of claim 1, wherein A is 1,4-cyclohexanedimethanol or 1,6-hexanediol.

7. The polymer of claim 1, wherein the molecular weight is at least 10,000.

8. The polymer of claim 1, wherein the polymer is stable at 37° C. in an aqueous solution for at least 7 days.

9. The polymer of claim 1, wherein the polymer is biodegradable.

10. A method of preparing a polymer, the method comprising:
combining components comprising:
at least one hydroxy-containing compound of the formula (Formula I) HO—Z—OH, or
a mixture of Formula I and
(Formula Ia) HO—A—OH, and
at least one orthoester of the formula (Formula II)

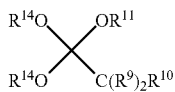

under conditions effective to polymerize at least a portion of the orthoester; and
removing byproducts comprising $R^{14}OH$;
wherein each $R^9$ and $R^{10}$ independently represents hydrogen or an organic group;
each $R^{11}$ and $R^{14}$ independently represents an organic group;
each A, optionally, is —C($R^1$)($R^2$)—(C($R^5$)$_2$)$_r$—C($R^3$)($R^4$)—, —Ar$^{het}$—, —Ar$^1$C($R^6$)($R^7$)—, a group of the formula (Formula III) —Ar$^2$—C($R^8$)$_2$—Ar$^2$—(B)$_m$—, —C(=O)—, —(C=O)—R—(C=O)— or combinations thereof;
R is an organic group;
each $R^1$, $R^2$, $R^3$, $R^4$, and $R^5$ independently represents hydrogen or an organic group, r is ( to 20, and one or more of R', $R^2$, $R^3$, $R^4$, and $R^5$ can optionally be joined with one another to form one or more rings;
Ar$^{het}$ represents a 1,2-heteroarylene group;
Ar$^1$ represents a 1,2- or a 1,3-arylene group, or a 1,2- or a 1,3-heteroarylene group, $R^6$ and $R^7$ independently represent hydrogen or an organic group, and $R^6$ and/or $R^7$ can optionally be joined with each other or with the Ar$^1$ group to form one or more rings;
each Ar$^2$ independently represents an arylene group, each $R^8$ independently represents an organic group, B represents an aromatic-containing organic group having a linking oxygen attached to the aromatic ring, and m =0 or 1; and
each Z is a therapeutic agent containing at least one phenoxy residue and at least one hydroxyl residue or at least a second phenoxy residue.

11. The method of claim 10, wherein Z is a Resveratrol or Curcumin residue.

12. The method claim 10, wherein A is 1,4-cyclohexanedimethanol or 1,6-hexanediol.

13. The method of claim 10, wherein the molecular weight of the polymer is at least 10,000.

14. The method of claim 10, wherein combining components further comprises combining an additional polymerizable compound selected from ketene acetals, monofunctional orthoesters, polyfunctional orthoesters, imagable compounds, compounds having latent reactive sites, or combinations thereof 15. A method of preparing a polymer comprising combining components comprising at least one hydroxy-containing compound of the formula (Formula I) HO—Z—OH or a mixture of Formula I and a compound of the formula (Formula Ia) HO—A—OH and at least one ketene acetal under conditions effective to polymerize at least a portion of the at least one ketene acetal, wherein the at least one ketene acetal is:
a compound of the formula (Formula IV)

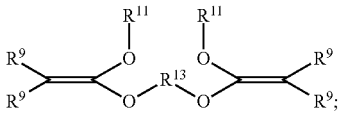

or
a compound of the formula (Formula V)

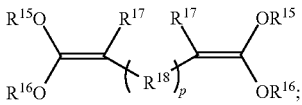

or
combinations thereof;
wherein:
each $R^9$ and $R^{17}$ independently represents hydrogen or an organic group;
each $R^{11}$, $R^{13}$, $R^{15}$, and $R^{16}$ independently represents an organic group;
$R^{18}$ represents oxygen or an organic group and p =0 or 1;
each $R^{11}$ can optionally be joined with $R^{13}$ to form one or more rings;
geminal $R^{15}$ and $R^{16}$ groups can optionally be joined to each other to form rings;
each A, optionally, is —C($R^1$)($R^2$)—(C($R^5$)$_2$)$_r$—C($R^3$)($R^4$)—, —Ar$^{het}$—, —Ar$^1$C($R^6$)($R^7$)—, a group of the formula (Formula III) —Ar$^2$—C($R^8$)$_2$—Ar$^2$—(B)$_m$—, —C(=O)—, —(C=O)—R—(C=O)—, or combinations thereof;
R is an organic group;

each $R^1$, $R^2$, $R^3$, $R^4$, and $R^5$ independently represents hydrogen or an organic group, r is 0 to 20, and one or more of $R^1$, $R^2$, $R^3$, $R^4$, and $R^5$ can optionally be joined with one another to form one or more rings;

$Ar^{het}$ represents a 1,2-heteroarylene group;

$Ar^1$ represents a 1,2- or a 1,3-arylene group, or a 1,2- or a 1,3-heteroarylene group, $R^6$ and $R^7$ independently represent hydrogen or an organic group, and $R^6$ and/or $R^7$ can optionally be joined with each other or with the $Ar^1$ group to form one or more rings;

each $Ar^2$ independently represents an arylene group, each $R^8$ independently represents an organic group, B represents an aromatic-containing organic group having a linking oxygen attached to the aromatic ring, and m =0 or 1; and each Z is a therapeutic agent containing at least one phenoxy residue and at least one hydroxyl residue or at least a second phenoxy residue.

16. The method of claim 15, wherein the compound of the formula (Formula IV) is represented by Formula IV(a):

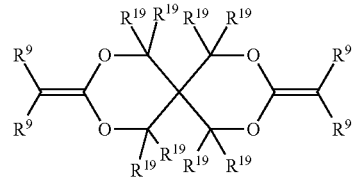

wherein each $R^9$ and $R^{19}$, independently represents hydrogen or an organic group.

17. The method of claim 16 wherein each $R^9$ and $R^{19}$ represents hydrogen.

18. The method of claim 15, wherein Z is a Resveratrol or Curcumin residue.

19. The method of claim 15, wherein A is 1,4-cyclohexanedimethanol or 1,6-hexandiol.

20. The method of claim 15, wherein the molecular weight of the polymer is at least 10,000.

* * * * *

UNITED STATES PATENT AND TRADEMARK OFFICE
CERTIFICATE OF CORRECTION

PATENT NO. : 8,106,146 B2  
APPLICATION NO. : 12/766676  
DATED : January 31, 2012  
INVENTOR(S) : Michael Eric Benz, Lian Leon Luo and Erica TenBroek It is certified that error appears in the above-identified patent and that said Letters Patent is hereby corrected as shown below:

| | | | |
|---|---|---|---|
| Title page, item (75) Inventors: | Lian Leon | should be | Lian Leon Luo |
| Column 37, Line 56: | ... $POE_T$ | should be | ...$POE_1$... |
| Column 38, Line 22: | ...$(C(R^5)_2)^r$,... | should be | ...$(C(R^5)_2)_r$... |
| Column 39, Line 4: | ...thereof | should be | ...thereof. |
| Column 39, Line 62: | ...r is ( to 20,... | should be | ...r is 0 to 20,... |
| Column 39, Line 63: | ...one or more of R',... | should be | ...one or more of $R^1$,... |
| Column 40, Line 23: | ...thereof | should be | ...thereof. |
| Column 40, Line 62: | ...$(C(R^5)_2)^r$... | should be | ...$(C(R^5)_2)_r$... |

Signed and Sealed this  
Eighth Day of May, 2012

David J. Kappos  
*Director of the United States Patent and Trademark Office*